(12) United States Patent
Podmore et al.

(10) Patent No.: US 11,013,527 B1
(45) Date of Patent: May 25, 2021

(54) CELLULITE TREATMENT SYSTEM AND METHODS

(71) Applicant: NC8, Inc., Mountain View, CA (US)

(72) Inventors: Jonathan Podmore, San Carlso, CA (US); Earl Bright, II, Sunnyvale, CA (US); Joshua Makower, Los Altos Hills, CA (US); John Hanley, Manhattan Beach, CA (US); Pablo Acosta, Newark, CA (US); Theodore Ketai, Chico, CA (US); William Sauway Law, Palo Alto, CA (US); Michael Schaller, Louisville, CO (US); Bryan Hartley, Redwood City, CA (US)

(73) Assignee: NC8, Inc., Mountain View, CA (US)

( * ) Notice: Subject to any disclaimer, the term of this patent is extended or adjusted under 35 U.S.C. 154(b) by 0 days.

(21) Appl. No.: 17/177,271

(22) Filed: Feb. 17, 2021

Related U.S. Application Data

(63) Continuation of application No. 17/154,232, filed on Jan. 21, 2021, which is a continuation-in-part of application No. PCT/US2019/042871, filed on Jul. 22, 2019.

(60) Provisional application No. 62/702,314, filed on Jul. 23, 2018, provisional application No. 62/736,016, filed on Sep. 25, 2018, provisional application No. 62/798,515, filed on Jan. 30, 2019, provisional application No. 62/802,368, filed on Feb. 7, 2019, provisional application No. 62/825,447, filed on Mar. 28, 2019.

(51) Int. Cl.
| | | |
|---|---|---|
| A61B 17/32 | (2006.01) |
| A61B 17/00 | (2006.01) |
| A61B 1/06 | (2006.01) |

(52) U.S. Cl.
CPC ........ *A61B 17/320016* (2013.01); *A61B 1/06* (2013.01); *A61B 2017/00747* (2013.01); *A61B 2017/00792* (2013.01)

(58) Field of Classification Search
CPC .......... A61B 2017/00747; A61B 2017/00792; A61B 17/320016; A61B 1/06
See application file for complete search history.

(56) References Cited

U.S. PATENT DOCUMENTS

| | | | |
|---|---|---|---|
| 5,478,347 | A | 12/1995 | Aranyi |
| 5,649,947 | A | 7/1997 | Auerbach et al. |
| 5,728,112 | A | 3/1998 | Yoon |
| 5,749,147 | A | 5/1998 | Hasegawa |
| 6,377,854 | B1 | 4/2002 | Knowlton |
| 7,217,265 | B2 | 5/2007 | Hennings et al. |
| 7,442,192 | B2 | 10/2008 | Knowlton |
| 7,671,423 | B2 | 3/2010 | Voldman |

(Continued)

FOREIGN PATENT DOCUMENTS

| | | |
|---|---|---|
| CN | 201617909 | 11/2010 |
| CN | 202154724 | 3/2012 |

(Continued)

*Primary Examiner* — Wade Miles

(57) ABSTRACT

Systems and methods for treating cellulite including an apparatus that applies or a method involving separating septa to eliminate or reduce the appearance of cellulite. In one approach, an interventional tool is placed between tissue layers to engage and treat septa connecting tissue layers between which fat deposits are contained.

19 Claims, 35 Drawing Sheets

(56) References Cited

U.S. PATENT DOCUMENTS

| | | | |
|---|---|---|---|
| 7,871,423 B2 | 1/2011 | Livneh | |
| 8,167,280 B2 | 5/2012 | Chomas et al. | |
| 8,348,867 B2 | 1/2013 | Deem et al. | |
| 8,439,940 B2 | 5/2013 | Chomas et al. | |
| 8,652,123 B2 | 2/2014 | Gurtner | |
| 8,979,881 B2 | 3/2015 | Clark, III | |
| 9,358,033 B2 | 6/2016 | Ballakur et al. | |
| 9,539,439 B2 | 1/2017 | Jones et al. | |
| 9,615,882 B2 | 4/2017 | Shroff et al. | |
| 9,919,168 B2 | 3/2018 | Altshuler et al. | |
| 9,974,519 B1 | 5/2018 | Schwarz et al. | |
| 10,117,892 B2 | 11/2018 | Perry | |
| 10,271,866 B2 | 4/2019 | Clark, III | |
| 2003/0130628 A1 | 7/2003 | Duffy | |
| 2003/0158566 A1 | 8/2003 | Brett | |
| 2004/0243159 A1 | 12/2004 | Shiuey | |
| 2004/0260210 A1 | 12/2004 | Ella et al. | |
| 2005/0251120 A1* | 11/2005 | Anderson | A61F 7/00 606/20 |
| 2006/0172255 A1 | 8/2006 | Hochman et al. | |
| 2006/0241663 A1 | 10/2006 | Rice et al. | |
| 2006/0241673 A1 | 10/2006 | Zadini et al. | |
| 2008/0015624 A1 | 1/2008 | Sonoda et al. | |
| 2008/0058603 A1 | 3/2008 | Edelstein et al. | |
| 2008/0109023 A1 | 5/2008 | Greer | |
| 2008/0200863 A1 | 8/2008 | Chomas et al. | |
| 2009/0093737 A1 | 4/2009 | Chomas et al. | |
| 2009/0275899 A1 | 11/2009 | Deem et al. | |
| 2010/0106063 A1 | 4/2010 | Chomas et al. | |
| 2010/0228182 A1* | 9/2010 | Clark, III | A61B 18/20 604/21 |
| 2010/0237163 A1 | 9/2010 | Chomas et al. | |
| 2010/0256596 A1 | 10/2010 | Chomas | |
| 2011/0028898 A1 | 2/2011 | Clark, III et al. | |
| 2011/0295297 A1 | 12/2011 | Shirley et al. | |
| 2012/0022510 A1 | 1/2012 | Welches et al. | |
| 2012/0150208 A1 | 6/2012 | Messmer | |
| 2013/0123771 A1 | 5/2013 | Clark, III et al. | |
| 2013/0190739 A1 | 7/2013 | Clark, III et al. | |
| 2013/0190740 A1 | 7/2013 | Clark, III et al. | |
| 2013/0197427 A1 | 8/2013 | Merchant et al. | |
| 2014/0276693 A1* | 9/2014 | Altshuler | A61B 18/20 606/14 |
| 2018/0116905 A1 | 5/2018 | Capelli et al. | |
| 2018/0214169 A1 | 8/2018 | Gutwein et al. | |
| 2019/0046738 A1 | 2/2019 | Banker | |
| 2020/0046391 A1 | 2/2020 | Capelli et al. | |

FOREIGN PATENT DOCUMENTS

| | | |
|---|---|---|
| CN | 2504047 | 10/2012 |
| CN | 202821527 | 3/2013 |
| CN | 204191319 | 3/2015 |
| CN | 104644244 | 5/2015 |
| CN | 204500879 | 7/2015 |
| GB | 2350080 A | 11/2000 |
| WO | WO2019060924 | 3/2019 |

* cited by examiner

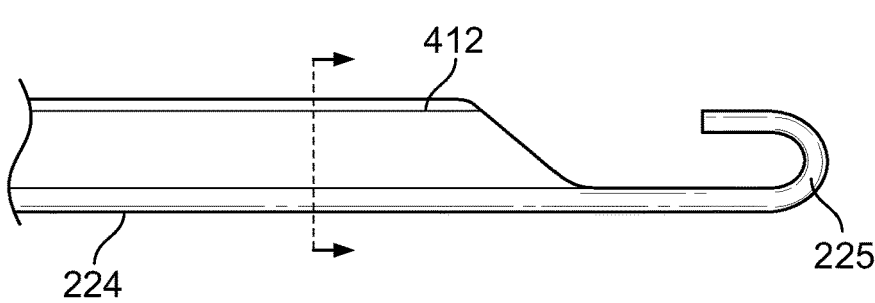
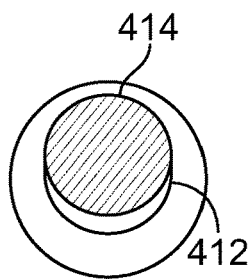
FIG. 7T
FIG. 7U
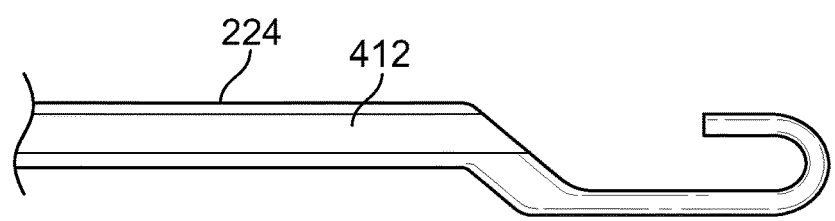
FIG. 7V
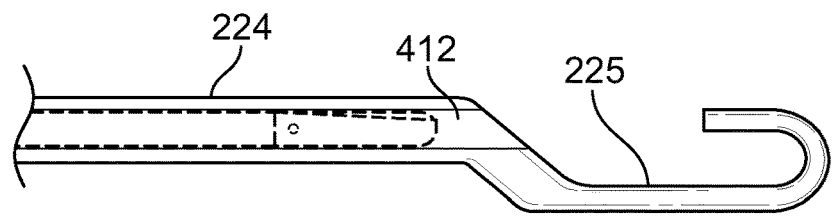
FIG. 7W
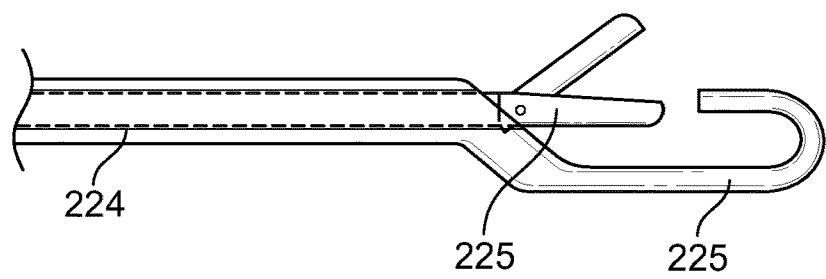
FIG. 7X

CELLULITE TREATMENT SYSTEM AND METHODS

This application is a continuation of U.S. application Ser. No. 17/154,232, filed Jan. 21, 2021; and claims the benefit and priority of PCT/US19/42871, filed Jul. 22, 2019 and U.S. Patent Application No. 62/702,314 filed Jul. 23, 2018; 62/736,016 filed Sep. 25, 2018; 62/798,515 filed Jan. 30, 2019; 62/802,368 filed Feb. 7, 2019; and 62/8254,447 filed Mar. 28, 2019, the entirety of the contents of which are hereby incorporated by reference.

FIELD OF THE DISCLOSURE

The present disclosure generally relates to systems and methods for treating cellulite.

Background of the Disclosure

There is a continuing need for an effective approach to treating cellulite, also known as gynoid lipodystrophy, nodular liposclerosis, edematofibrosclerotic panniculopathy, panniculosis, adiposis edematosa, demopanniculosis deformans or status protrusus cutis. Moreover, there is a need for proactive treatment modalities that prevent future or reoccurrence of cellulite and which are easy and effective to use.

It has been reported that more than 85% of women have cellulite thus suggesting that cellulite is a physiologic rather than pathologic condition. The existence of fat in the reticular dermis alone is not thought to cause cellulite. Cellulite can be described as the herniation of subcutaneous fat within fibrous connective tissue that is expressed as dimpling of the skin. This fat loading can lead to stress on connective tissue located between fat lobulas. Such dimpling is more common in women than men due to the orientation of subcutaneous fibrous structures defining chambers containing fat cells. In fact, it is this structure that is believed to cause the appearance of cellulite more than being overweight. Often, cellulite appears on the pelvic region including the buttocks, lower limbs and abdomen.

Subdermal fat layers below the epidermis are contained between dermal layers connected by septa which act as connective tissue between the dermal layers. In men, the septa are arranged more randomly and densely oriented in a more criss-crossed configuration while the septa in women are generally more parallel in arrangement. Also, men have thicker dermis and more angled septa relative to the skin surface whereas women have relatively thinner dermis which thins with age, and septa that are perpendicular to the skin surface. Moreover, women with cellulite have exhibited thickening of the septa in the regions of cellulite and tensioning of septa highlights cellulite. In women, fat storage in adipose tissue has a biological purpose in that it is maximized ensuring adequate caloric availability for pregnancy and lactation. An increase in fluid retention or proliferation of adipose tissue in such subdermal fat layers can further result in the appearance of cellulite where the septa is maintaining a first distance between dermal layers, thus creating dimples, whereas pockets between septa bulge. Over time, the septa may stretch, then eventually contract and harden thus retaining tissue layers at fixed distances, but pockets between such septa may be expanded thus adding to the appearance of cellulite.

Various approaches have been taken to treat or address cellulite. Early treatments involved attempts at increasing circulation and fat oxidation in areas exhibiting cellulite. Here, substances such as hyaluronic acid and aminophylline were injected in the target areas to reduce cellulite. Other approaches involved electroporating the target areas followed by the application of mesotherapy, or applying dermological creams or other supplements to cellulite. These approaches could be supplemented by massage or massage was used alone for the purpose of promoting increased fat reabsorption or drainage of fluids and toxins in the treated areas. Ultrasound has also been proposed to disrupt subcutaneous tissues and fat and has been used in combination with liposuction. Low acoustic pressure in combination with the infiltration of microbubbles has also been employed to reduce the appearance of cellulite, as has the use of other energies such as lasers and radio frequency. Such approaches have been characterized by limited or unpredictable results. More recently, the cutting of septa with blades or needles in the subdermal region has been employed. Prior approaches have been found to be labor intensive and very traumatic to the tissue leading to bleeding, bruising, tough tissue nodules, long, painful recoveries and inconsistent results.

Accordingly, there is a need for effective and efficient approaches to treating, minimizing or eliminating cellulite with simple systems that minimize trauma. These approaches should be associated with predictable results and be relatively easy to employ.

The present disclosure addresses these and other needs.

SUMMARY OF THE DISCLOSURE

Briefly and in general terms, the present disclosure is directed towards cellulite treatment systems and methods involving an apparatus that facilitates and methods involving, depending on the system used and force applied by the user, stretching, re-orienting, disrupting, cutting, slicing, and/or tearing septum or septa in a location of cellulite. In one aspect, the treatment approach involves a tissue cutting or slicing system.

In one embodiment, a cellulite treatment device is mounted at a distal end portion of a shaft and is sized and shaped to be advanced between tissue layers. In one particular aspect, fibrous septa that connect superior and inferior fascia plateaus within skin can be crossed with the treatment device using one or more of an array of tools to engage, and depending on the tool used and force applied by the user, stretch, re-orient, tear, disrupt, cut or slice septa. By doing so, the target subcutaneous connective tissue associated with the surface defect can be directly modified with minimal impact to surrounding blood vessels and lymphatic system and fat can be more evenly distributed and skin can assume a smoother appearance.

In one or more aspects, a cellulite treatment system embodies a tool facilitating an ability to reach and treat all target cellulite appearance areas through a single or a limited number of entries through the skin. In certain aspects, such tool is sized, shaped and configured (e.g. less than or equal to about two millimeters diameter and blunt dissection tip) to be placed within and advanced between tissue layers on its own and without assistance from external skin stabilizing structure, such as a suction device. Entry points through the skin such as high on the hip under where a bikini or underwear strap would be and along creases or transitions between buttocks and thighs are employed. Identification and assessment of target septa is accomplished by pushing, pulling or otherwise tensioning septa in areas believed to be associated with the expression of cellulite on the outside of skin. It has been recognized that septa causing a dimple or depression are located at various angles and locations relative to the dimple or depression observed on the skin and are not necessarily directly below such expressions of cellulite, and the treatment system and method is configured to identify the septa responsible for the appearance of cellulite that has been marked on the skin and target treatment on those septa and leave adjacent septa, blood vessels, etc. intact. Moreover, a range such as a small subset or a larger number of septa can be the structure causing a particular depression or dimple.

In one method, anesthetic is injected into the treatment site transcutaneously or subcutaneously, a cellulite treatment system is inserted subcutaneously across the treatment site and used to identify the septa responsible for a depression or dimple by pushing or pulling on various septa to cause a depression in the skin in the target area, and a cutting or slicing device or septa disruption structure is placed subcutaneously at the treatment site and employed to engage and cut or slice or break the septa tissue. In one particular aspect, the patient is directed to clench their buttocks and/or leg muscles to help facilitate identifying target areas and after septa treatment confirm release of septa that create dimples or depressions. Alternatively, the physician can press in a cranial to caudal direction on the skin above the treatment target or pull from below the treatment target. Remote imaging or ultrasonic or fluoroscopic energy can be employed to observe the procedure. A resizing or alternative configuration of the treatment structure can be employed to complete the treatment of a particular area. The treatment device is then repositioned to treat additional areas. The treatment device can be configured to treat a plurality of areas simultaneously or in succession without removing from the patient or a spot treatment approach can be taken. Langer lines can be employed as a reference to direct treatment. Additionally, through one or more entry points, various treatment trajectories are directed and in certain applications a steerable introducer is used to access treatment areas. Further, anti-inflammatory, collagenase, deoxycholic acid, salicylic acid, glycolic acid, hyaluronic acid or cellulite treatment medicants can be employed at the interventional site separately or directly by the interventional device or other procedural instrumentation. Aspects of the current invention include specific identification of the septa responsible for the cellulite appearance, severing or separation of those septa, confirmation intra-operatively of the separation of those septa was accomplished and the prevention of the re-appearance of the cellulite.

In various aspects, the treatment device can include one or more of blunt tipped scissors, a guillotine-type angled blade, projecting linkages, side opening hooks or V-shaped structure, an internal hook, a bevel hook, a rotating structure or blade, a cutting balloon or harmonic scalpel, selective cautery structure or energy transmitting structure for disrupting, cutting, slicing or dissecting tissue and/or controlling bleeding. In one particular approach, the treatment device includes a mechanical septa cutting element, such as a blade or sharpened surface, that cooperates with a septa hooking element to both hook then cut, slice, tear or disrupt septa. One or more of the septa hooking element and the septa cutting element is convertible from a hooking configuration to a cutting configuration and from a cutting configuration to a hooking configuration or to a stored configuration. In another particular approach, the treatment device is embodied in an elongate member insertable through the skin capable of expanding at least one region from a smaller state to a wider state, and when in the wider state is configurable to both hook and cut, slice or disrupt target septa. In one or more alternative or additional aspects, cutting or disruption is accomplished with electrical or thermal means such as mono-polar or bi-polar structures or a hot wire configured to address bleeding and ease cutting.

The cellulite treatment system also involves in certain approaches, illumination such as a bright light configured at or emitted through a tip of treatment structure or placed along or at strategic locations along treatment structure for the purposes of tracking advancement of the tool to the treatment site and locating intra-dermal structures at the treatment site. In this way, direct observation of the treatment device by transillumination through the skin is provided and positioning and performance thereof subcutaneously is readily available to an operator.

Moreover, objective measurement devices are included in the treatment system to assess the results of therapy. In one approach, laser light energy such as bright light or laser light is emitted and received by the measurement device and surfaces of treated areas is scanned. The measurement device creates a complete three-dimensional map of all cellulite relative to normal skin. By comparing improvement of volume of divots versus normal idealized surfaces, the operator can calculate total and local volume benefits of therapy and track improvement over time.

Additionally, the disclosed devices and structures are employed for body sculpting, eliminating wrinkles, treating acne scars and/or repositioning skin. Foam fillers or spacers of varying lengths and other structures such as subcutaneous attachment structures that are absorbable or permanent are used to accomplish such objectives.

These and other features of the disclosure will become apparent to those persons skilled in the art upon reading the details of the systems and methods as more fully described below.

DETAILED DESCRIPTION OF THE DISCLOSURE

Before the present systems and methods are described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the disclosure. The upper and lower limits of these smaller ranges may independently be included or excluded in the range, and each range where either, neither or both limits are included in the smaller ranges is also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the present disclosure, the preferred methods and materials are now described.

It must be noted that as used herein and in the appended claims, the singular forms "a", "an", and "the" include plural referents unless the context clearly dictates otherwise. Thus, for example, reference to "the system" includes reference to one or more systems and equivalents thereof known to those skilled in the art, and so forth.

Figure 1A:
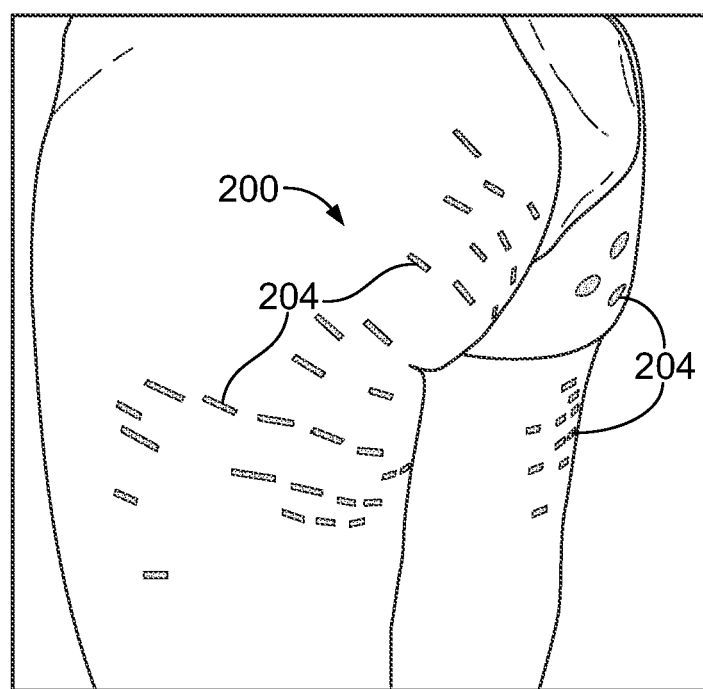
FIGS. 1A and B are perspective views, depicting cellulite on a subject's skin and a plan for treating the cellulite.
Figure 1B:
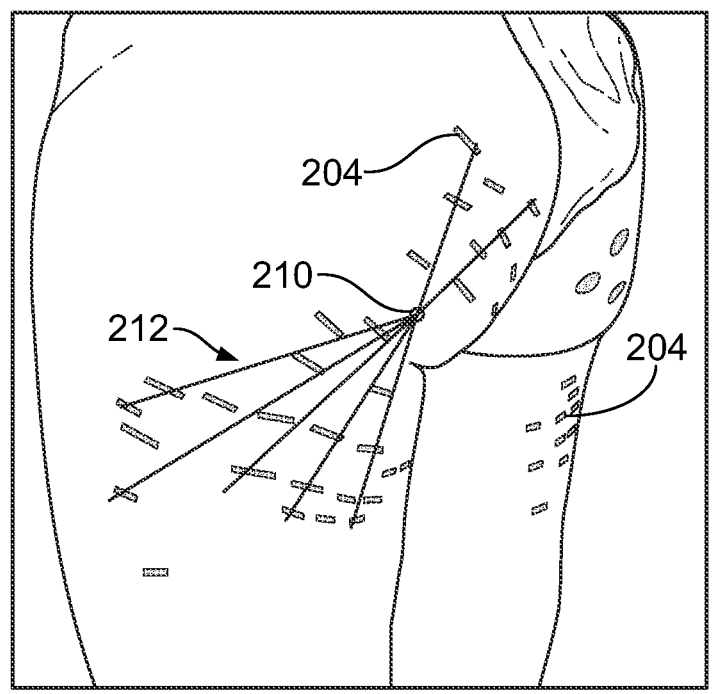
FIG. 1C is a top view, depicting treatment across and along Langer lines of a subject lying on a treatment table.
FIG. 1D is a top view, depicting a cellulite treatment assembly and approach for treating cellulite.
FIGS. 1E-N are partial cross-sectional views, depicting on embodiment of treating septa below a skin surface.
FIGS. 1O-R are side views partially in cross-section, depicting an alternative approach to transillumination.

With reference to FIGS. 1A-B, there is shown a person exhibiting cellulite 200 about their thighs and buttocks. In one approach to treatment, dimples and/or depressions characteristic of the cellulite 200 intended to be treated are identified or circled with markings 204, preferably while the patient is standing as for most patients the appearance of their cellulite disappears when they lie down on their stomach because gravity is pulling in a different direction. In another embodiment, computerized imaging equipment is used to locate and mark dimples and/or depressions. In FIGS. 1A-B, forty-four dimples and depressions are marked for possible treatment. The physician treating the patient determines an instrument insertion site 210 and paths 212 that most efficiently treat cellulite with a minimal amount of insertion sites and instrument paths under the skin. Preferably, an instrument insertion site is chosen that is in a crease or fold of skin such as where the buttocks meets the thigh or in the crease between the two buttocks at a location that is not seen when the buttocks are in natural contact for improved cosmesis after the procedure healing period. In certain patients, the inner thigh is chosen as an insertion site as this location is less visual as it heals. Such treatment paths are selected by the operator preferably using a straight edge that bends or contours to the patient or can be generated automatically by employing a computerized controller programmed to most efficiently address and measure cellulite residing in a pre-defined treatment site. The computerized controller can be associated with a scanner that identifies specific dimples and areas for treatment such as by employing laser technology. In this regard, the computerized controller includes a program specific to cellulite treatment and is used in conjunction with an electronic and mechanical device and comprises or includes a non-transitory computer-readable storage medium and a computer-program mechanism embedded therein to both identify treatment areas and to plot primary and alternative approaches to treatments. In another embodiment, computerized visualization and treatment planning equipment is used to assist the physician in determining insertion site locations and paths to be taken to the marked targets.

Once a treatment approach is planned, the patient lies down on their stomach on the treatment table. Alternatively, because of the minimally invasiveness of the current approach, a patient can be treated while standing, particularly for a small number of treatment targets, or while standing and leaning forward on a support and alternatively between standing and leaning forward so that gravity can help identify and confirm treatment of the targeted septa. Moreover, the measurement device creates a complete three-dimensional map of all cellulite relative to normal skin. By dating and comparing improvement of volume of divots or dimples versus normal idealized surfaces, the operator calculates total and local volume benefits of therapy and track improvement over time.

Figure 1C:
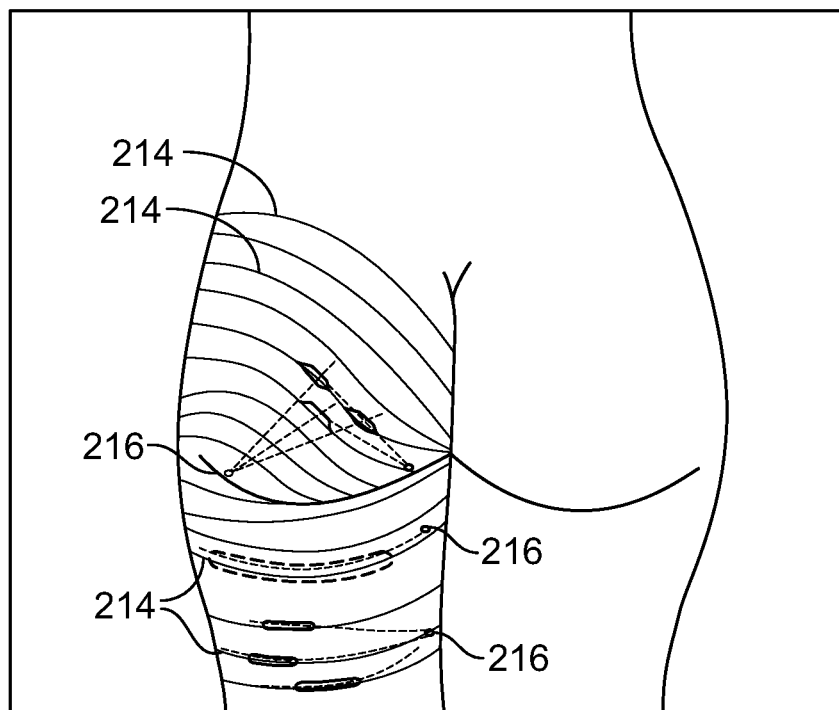

In one specific approach, as shown in FIG. 1C, the cellulite treatment follows or references Langer lines 214 existing in tissue. Langer lines 214 correspond to natural orientations of tissue fibers that exist in humans, and have been recognized as being generally parallel to the orientation of muscle fibers. The Langer lines 214 can be used as a reference to treat cellulite. Notably, cellulite appears to be related to and fall along the locations of Langer lines. In one approach, multiple treatment targets along Langer lines are treated from a single entry 216, the Langer lines 214 providing a map along which treatment is accomplished. Thus, treatment can be directed along Langer lines 214 as shown on the thigh for illustrative purposes to treat targeted septa, or additionally or alternatively, treatment can be transverse to Langer lines 214 as shown on the buttock for illustrative purposes to treat targeted septa. Treatment can also be directed at various positions about connecting tissue or septa. That is, septa can be engaged, stretched, re-oriented, torn, cut, sliced, ruptured or disrupted from various sides or angles respecting septa. Thus, septa can be treated from above, below or the sides of septa to achieve the best results. For example, in a particular situation, treatment can be most effective from above a particular connecting tissue to take advantage of gravity where treatment forces placed on the connecting tissue coincide with the direction of gravity or the direction that gravity most often works on a standing body, as it has been observed that cellulite is often most visible in a standing individual.

Figure 1D:
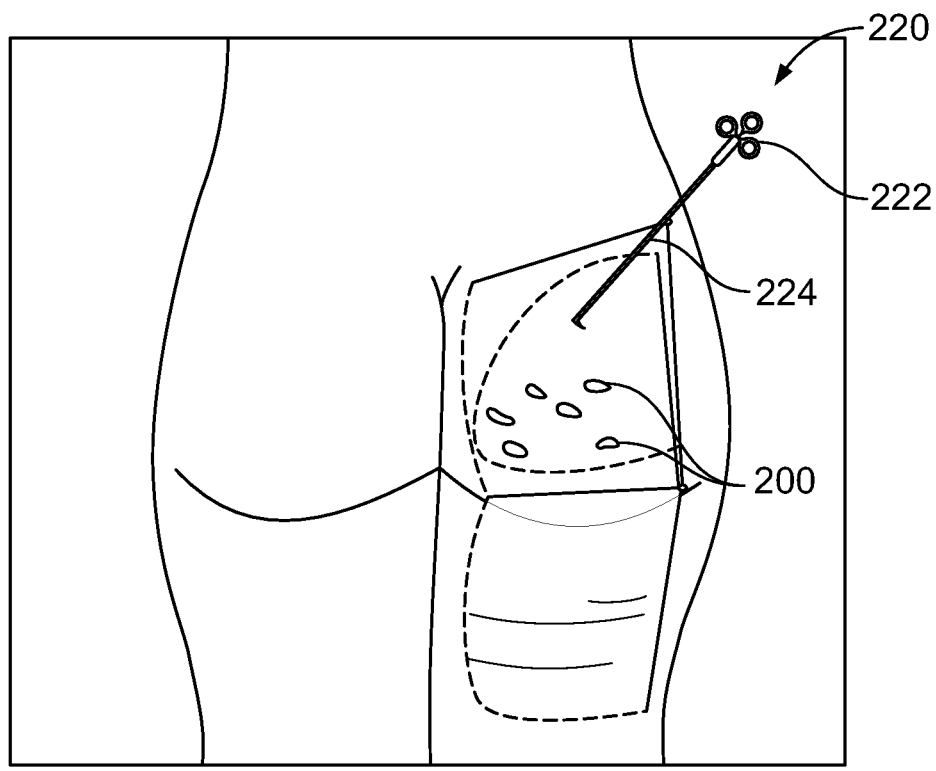

Turning now to FIG. 1D, there is shown a cellulite treatment assembly 220 including a handle 222 and an elongate member or needle-sized structure preferably two millimeters or less in diameter, like structure 224 extending longitudinally therefrom. A force gauge (electronic or mechanical) can be provided to ensure that a pre-determined amount of force would be applied to the tissue when testing the septa to prevent over or under pulling. A treatment device 225 capable of one or more of engaging, stretching, slicing, cutting or disrupting connective tissue is configured at a distal end portion of the elongate member 224 (e.g., FIGS. 1E-N). All cutting means can be combined with or further energized with RF, a laser, ultrasonic or thermal energy to produce cutting and coagulation together or separately. In certain aspects, there can be a single entry site or two entry sites, one high on the hip and another along the crease or transition between the buttocks and thigh, or at the inner thigh. Such locations are characterized in that they can be easily hidden either naturally or by clothing. Treatment targets, depressions and dimples that have been marked on the skin surface while the patient is standing often go away when the patient lies down on their stomach because gravity acts on the skin and underlying connective tissue in a different direction such that the ink mark is apparent but the dimple or depression is not. The disclosed interventional devices are configured such that a user can approach a target location and first use the interventional device to push, pull or otherwise tension septa in a target area under the skin to identify the specific septa impacting the target and/or which is the cause of the expression of cellulite. In other words, pulling or pushing on the septa under the skin to find the one(s) that create the dimple or depression in the skin surface. For some treatment targets, taking an approach from an entry located inferior the treatment target, advancing the end of the interventional device beyond the treatment target and then pulling inferiorly (effectively the "down" direction if the patient was standing) can provide a better approach, for example, for treatment targets on the leg, to re-create the dimple when the patient is lying down. One or more strain gauges can be incorporated within the treatment device to help identify target septa as well as to assess the progress and completion of treating septa. This facilitates targeting of key septa in a less impactful way, ideally minimizing bruising or other issues associated with cutting or disrupting a large area around the target. There are thus herein shown various approaches to treating cellulite expressed as dimples or depressions 200 in the skin surface. Moreover, the handle portion can be employed to create an indentation in skin through which interventional devices can be inserted subcutaneously. A treatment regimen is selected for inserting interventional instruments based upon the subject's anatomy as it relates to the septa 350 connecting tissue layers that define the chambers retaining fatty or other tissues. If desired, while anesthetic and/or sedation is taking effect, ultrasound can be used to assess the subcutaneous trajectory and depth of the various connective tissue bands responsible for the surface unevenness. The ultrasound evaluation can help with the particular trajectory selected for the desired depth. The ultrasound evaluation can also help with positioning the distal end portion of the treatment instrument strategically at the connection point between the connective tissue and the dermis or the facia.

Figure 1E:
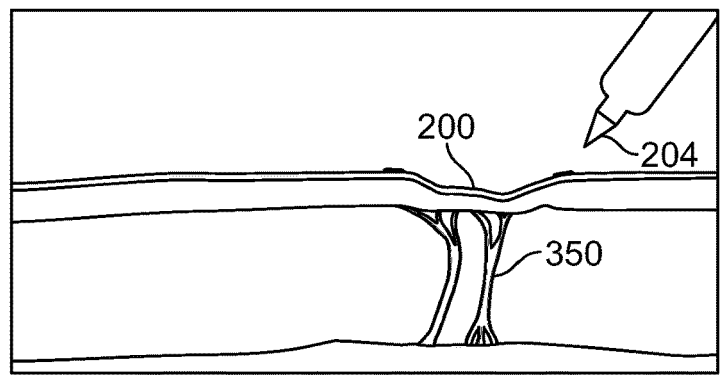
Figure 1F:
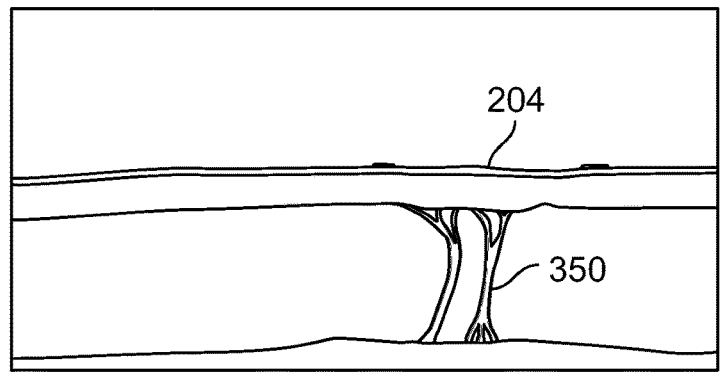
Figure 1G:
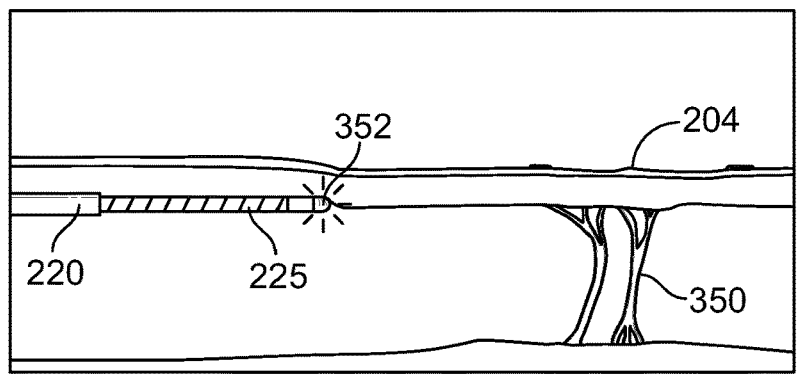

As shown in FIG. 1E, targeted locations of cellulite 200 to be treated are marked 204 on the surface of the skin. This can be done when the patient is standing to best see cellulite. As shown schematically in FIG. 1F, cellulite can diminish or disappear when an individual is laying down, and should this happen, the marks identify and confirm their locations.

In one aspect, a distal end portion of a cellulite treatment assembly 220 is inserted through the skin and the blunt tip is guided up into close proximity of the dermis as the tip can be tracked as it is advanced toward septa 350 (FIG. 1G) near the marked location 204. The inventors have discovered given the elasticity of septa 350, the distance from the marked location 204 to where the treatment assembly 220 is inserted into the skin is preferably at least about 2 cm so that there is enough distance to pull and disrupt septa 350 and not have the tip of the cellulite treatment assembly exit the skin in the process. Additionally, a depth below the skin where septa 350 is preferably engaged (i.e., cut, sliced, torn, stretched, re-oriented (e.g. criss-crossing) or disrupted) is identified and determined. After determining the subcutaneous depth to be accessed for the cutting, slicing, tearing, stretching, re-orienting (e.g. criss-crossing) or disrupting of septum 350, the cellulite treatment assembly or other tool with a sharpened or blunt tip is inserted through the skin, advanced between subcutaneous tissue layers and toward septa 350. In one approach, a distal end portion of the cellulite treatment assembly is configured with an illuminated tip 352 with enough brightness to be seen through the skin. The intensity of light emitted by the tip 352 can be set to a specific constant level such that at the preferred depth below the skin for severing or otherwise engaging septa 350, the light that appears at the level of the skin as a circle or projection is of a pre-determined size. Thus, the treatment device is advanced to the target site. At the target site, the user adjusts the depth of the tip of the treatment tool such that the circle or projection of light is the pre-determined size. The septa 350 is tested and if confirmed as a target for treatment, the septa 350 is treated while maintaining the circle or projection at the pre-determined size. The user can also use the size of the circle or projection of light to maintain the depth of the tip of the treatment tool as it is advanced under the skin to the treatment target. In an alternative or another aspect, a sharpened tip is employed to create access to target tissue thus allowing the tool to create the desired path both into tissue as well as between tissue layers. It is expected that the depth that these tools are advanced will be between about 3 and about 10 mm below the skin surface, but it is anticipated that lesser and greater depths may also be optimal for a particular subject. In any event, the depth selected is chosen for cutting, slicing, disrupting, tearing, stretching or re-orienting of the subject's septa 350. Moreover, in one embodiment, it is to be appreciated that the device 220 is formed from a substantially rigid material so that a consistent plane below the skin surface is accessed.

Figure 1H:
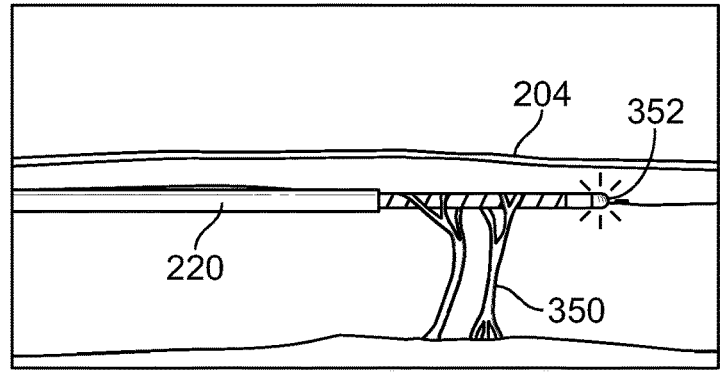
Figure 1I:
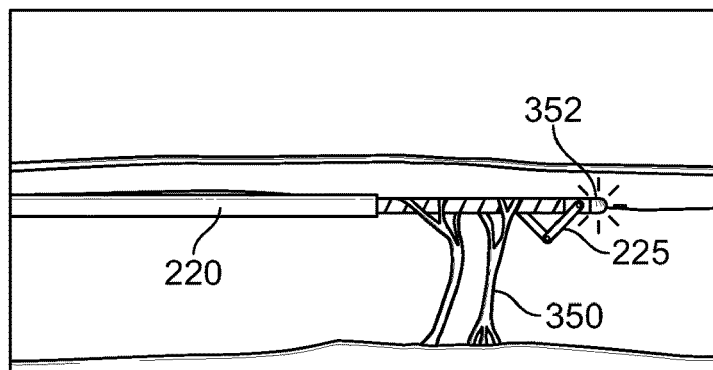
Figure 1J:
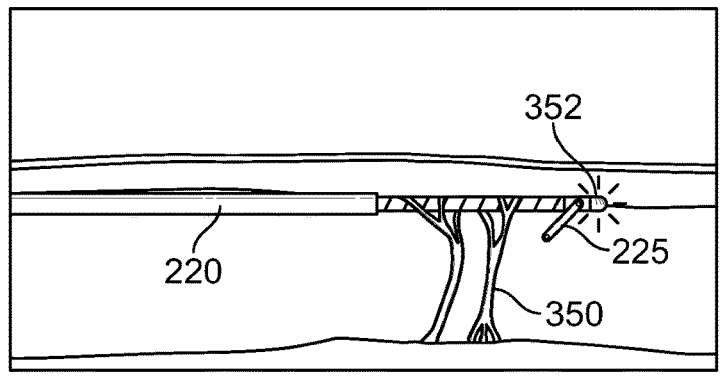
Figure 1K:
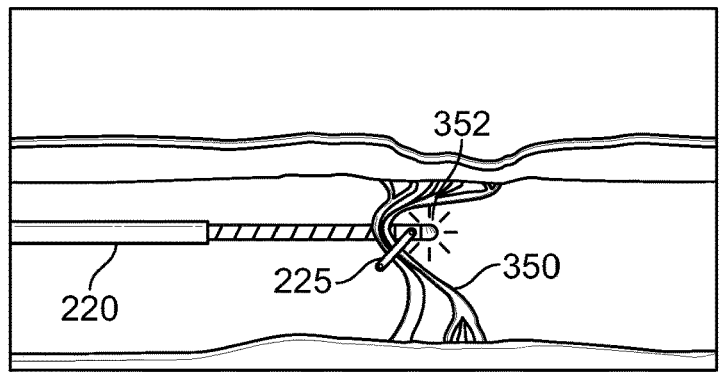

Using palpation, direct visualization (for example, transillumination or endoscopic) or non-invasive visualization (for example, ultrasound or fluoroscopic) or other means for determining the position of the interventional tool such as markings along the length of the instruments and its path within tissue, or providing the interventional instrumentation with radiopaque markers, the tool is placed at a site below where cellulite (for example a dimple) is seen on the subject's skin. The treatment device is advanced through septa 350 and to where the treatment device 225 is in a position best suited to accomplish the identification of target septa and the cellulite removal or minimization treatment. As shown in FIGS. 1H-J, in one approach, the treatment device 225 is passed beyond septa 350, a hook is deployed and then pulled proximally to tension septa 350, such as by hooking the septa (FIG. 1K). In another approach, the treatment device 225 is passed a few millimeters lateral, preferably about 1 to about 10 millimeters, more preferably about 3 to about 6 millimeters, and beyond the target location, a hook is deployed and then swept laterally toward the target followed by pulling proximally to hook and tension septa. During these and other steps, transillumination can be employed to track the treatment device and guide the procedure. The marks 204 can facilitate targeting of septa 350 while using transillumination to see the location of the treatment device 225. In other approaches, a separate device can be employed to engage septa 350 to see if such septa are the source of a dimple or depression expressed on the outside of the skin. Such a secondary device can be placed remotely from the target (i.e. lesion) and configured to be capable of applying tension to the surface of skin in a predetermined direction so as to create the effect of gravity and produce the visualization of the lesions while the patient is in a prone position (i.e. a broad region of adhesive attached to a spring mechanism such that a predetermined force would be applied relatively parallel to the surface of the skin in the direction the skin would move when standing in gravity). Using this additional device could further help the confirmation and location of lesions and allow confirmation that the treatment was effective. Also, in various approaches, a portion of the elongate member can be configured to transition from a smaller state to a wider or larger state, wherein in the wider or larger state a cutting surface (i.e. sharpened edge or energy) is presented to cut tissue, the device being sized and shaped to be inserted through the skin and engage one or more regions of septa subcutaneously.

Figure 1L:
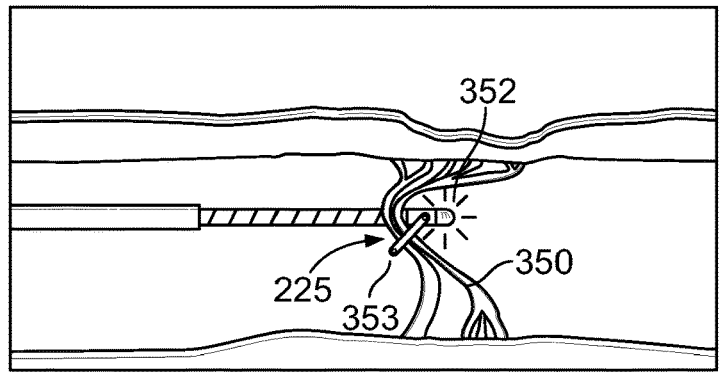

It is noted that septa causing a dimple or depression may be coming from various angles and locations relative to the dimple or depression seen on the skin rather than being directly below the dimple or depression, and may be due to one or only a few septa or a large number of septa that remotely cause the depression or dimple. Thus, so engaging certain septa will be reflected in some change in the dimple or depression on the skin. A determination is made concerning the correspondence with marks 204 made on the skin and the dimples being formed or re-formed. If the initial septa 350 that the user presses on or pulls on using the tool do not recreate a dimple or depression in the marked area 204, then the user releases those initial septa that were engaged and repositions the tool at different septa and presses on or pulls again. This is repeated until the septa responsible for a dimple or depression in the marked location are identified (FIG. 1K). Once proper septa are identified, the tool 225 is manipulated to cut, slice, disrupt, re-orient, stretch or tear septum 350 connecting tissue layers. In one approach, a blade 353 is deployed and presented for treatment (FIG. 1L). In another approach, a balloon (not shown) is inflated to disrupt the septa.

Figure 1M:
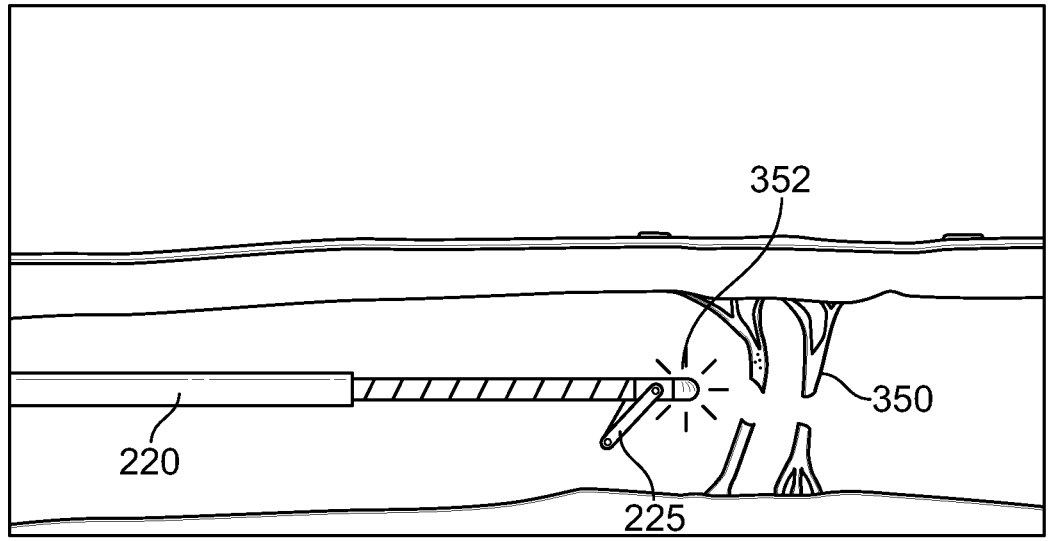
Figure 1N:
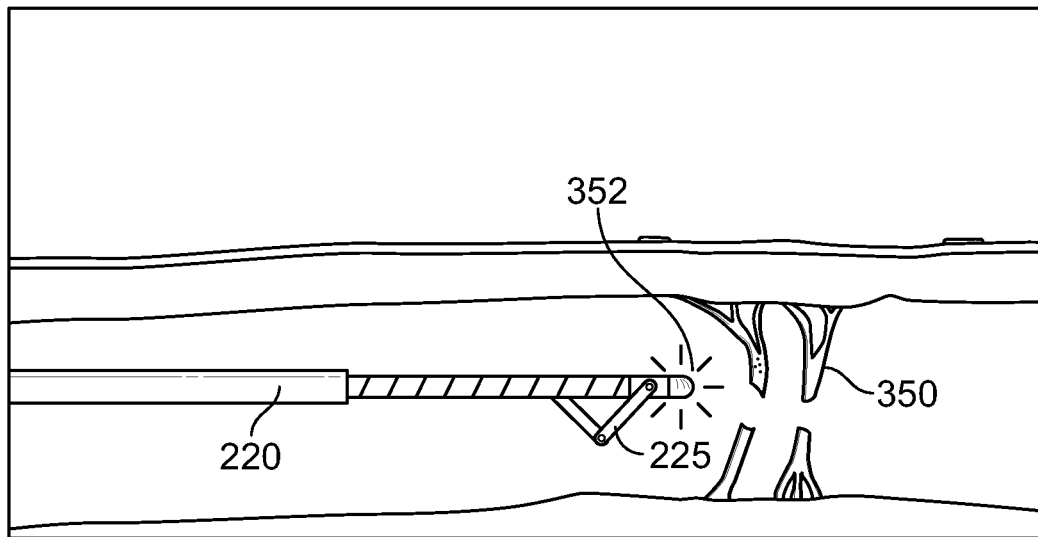
Figure 1O:
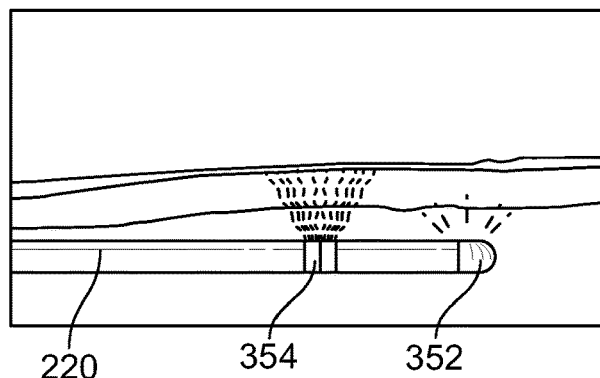

After the proper septa have been cut, sliced, disrupted, stretched, re-oriented or torn, the treatment element 225 is moved back to its initial collapsed configuration. The treatment element is then advanced beyond the marked treatment location, the treatment element (e.g., hook) is deployed and then pulled back under the marked treatment location to confirm that all of the septa responsible for causing the marked dimple or depression have been separated intraoperatively. If they have not been, the tool is manipulated to cut, slice, disrupt, stretch, re-orient or tear additional septa. The steps are repeated until all of the septa responsible for creating the marked dimple or depression have been severed or sufficiently stretched and the dimple or depression cannot be re-created intra-operatively using the tool. Such manipulation results in selective rupture, tearing, cutting or slicing of targeted septum 350, and the removal or minimization of dimples and the expression of cellulite on skin (FIG. 1M). Thereafter, the treatment element (e.g., hook and/or blade) is retracted back in (FIG. 1N partially collapsed) and the tool 220 is removed from the site to be withdrawn from the body or repositioned in any direction along and within the target tissue plane to treat additional areas.

Figure 1P:
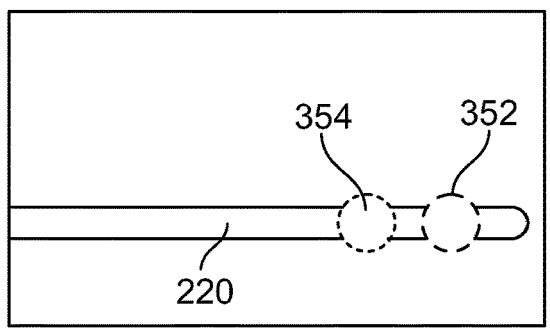
Figure 1Q:
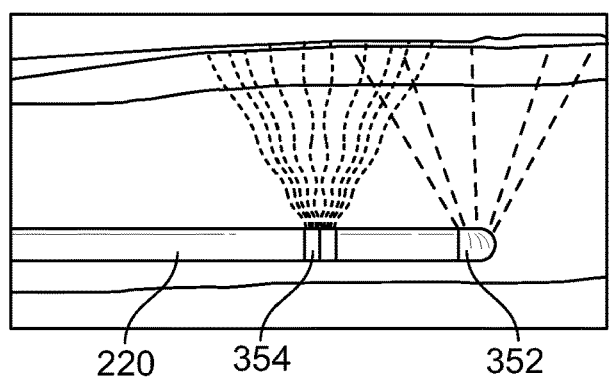
Figure 1R:
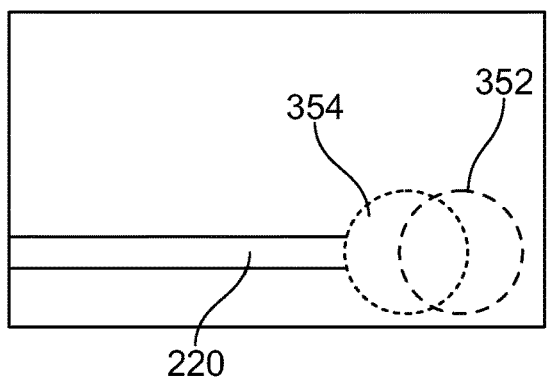

With reference to FIGS. 10-R, in additional or alternative approaches, a second light source 354 such as an LED (or other light source) is configured along the cellulite treatment assembly 220 proximal the illuminated tip 352 or alternatively, at the tip 352. In various approaches, a light source such as an LED chip can be configured at the tip of or otherwise along the treatment device with an electrical wire running proximally for control by the operator, or the light source can be generated by a light fiber extending along the device or to the tip with the LED or light source is configured within a proximally located position such as a handle of the treatment device. By so configuring such light sources 352, 354, the depth of the cellulite treatment assembly 220 within tissue can be assessed. As shown in FIGS. 10-P, when the cellulite treatment assembly 220 is placed within a first relatively shallow desired depth, the light sources 352, 354 appear spaced and define discrete patterns when viewing the light sources via transillumination through skin (FIG. 1P). When the cellulite treatment assembly 220 is placed deeper within tissue (FIGS. 1Q-R), the light sources 352, 354 overlap (FIG. 1R) due to the natural dispersion of light emitted from the light sources 352, 354. An operator of the treatment system can determine a depth of the cellulite treatment assembly 229 by noting the discrete patterns of light or the degree of overlap of light overlap, the dispersion of light emitted and intensity of the light emitted from the light sources 352, 354. Thus, allowing the operator to guide the distal end of the treatment assembly to the desired treatment location while maintaining the desired depth below the skin. The light sources 352, 354 can also be of a different color to aid in determining the orientation of the cellulite treatment system 220 within tissue through illumination. Moreover, the second light source 354 can emit a red color, for example, while the illuminated tip 352 can emit white light, while noting any variation of colors can also be employed. Also, the color of the light can change depending on the configuration of the treatment device, such as for example, the device can project a white or first color when sheathed or stowed and change to another color or second color when a portion of the device is deployed or before and after use such as when tissue is cut. A strain gauge can be configured to communicate and cooperate with the light source to sense loads placed on the treatment device during treatment to thereby facilitate a change in color of the light source and to signal the progress or completion of targeted treatment. Additionally, the second light source 354 can be employed via transillumination through skin to locate the cellulite treatment system relative to a treatment target area. Another benefit of the second light source is that it can indicate to the user where the hook and blade are located relative to the target septa. Also, as the treatment tool is being pulled proximally through the treatment target area, the illuminated tip 352 lets the user know when the hook and blade have been pulled through the target area. It is further noted that the light sources 352, 354 can be positioned at various alternative locations along a treatment device, and can be spaced from each other by various amounts. That is, a proximally positioned light source provides light proximal of the hook and blade of the treatment system, the same aiding the operator to assess and/or engage all septa at a target site. The operator can thus position the center of the light projected from the proximally positioned light source under and/or beyond the treatment target area to help ensure that the hook and blade of a treatment device, for example, deploys beyond the anticipated location of the target septa so that when the device is pulled proximally the hook or other tissue engaging structure of the treatment device encounters the target septa thus replicating the depression. Also, the cellulite treatment system can include greater than two light sources of the same or dissimilar colors. In another embodiment, different colors of light can be used to indicate that the state of the distal end of the instrument. For example, red light is used to indicate the hook and blade are inside the instrument for advancing under the skin, white light is then used to indicate the hook is deployed, and red light is then used to indicate when the blade is deployed.

After completing treatment of one target area, the procedure is repeated to treat other target areas. Accordingly, the same device can be employed to access tissue layers below other sites or depressions existing in skin. Notably, in one embodiment, the device is capable of anesthetic delivery as needed or desired when progressing to additional or new locations. There is thus provided a system configured to treat all target areas on the buttocks and thigh through a limited number of small entry sites, including through a single entry site. It is to be recognized that the system can further include structure permitting the assembly to be steerable to subcutaneous treatment sites. In such an embodiment, the device would be configured to define longitudinally flexible material, and the instrumentation would be steered to the desired position within tissue. Moreover, in certain applications, the device has a stiffness that varies along its length. In another embodiment, the treatment device is embodied in a deflectable catheter.

Moreover, in certain embodiments, the cellulite treatment system includes a squeezing tool that reproducibly applies lateral forces on the skin to emphasize the dimple or expression of cellulite so a before and after treatment effect can be obtained without requiring the patient to stand up and/or without having to remove the interventional tools. The squeezing tool can be embodied, for example, in a clamp with elongated feet on opposite sides thereof or includes four fingers that pull radially inward once deployed on the surface of the skin and activated over or adjacent the targeted cellulite region. Further, the patient is directed to clench their buttocks and/or leg muscles while lying on the procedure table or while standing to both identify treatment sites as well as confirm treatment. In another embodiment, a skin stabilizer, such as a suction stabilizer, can be used to help control the depth at which the cellulite treatment tool is advanced under the skin and maintain the targeted location as the tool is advanced.

Figure 2A:
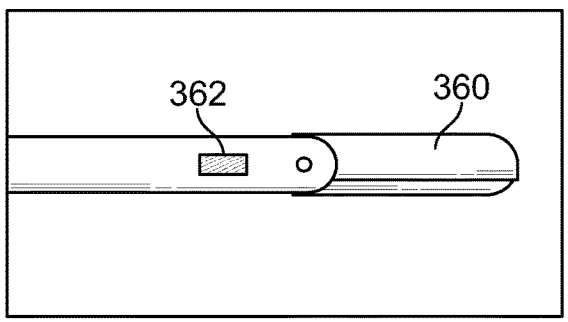
FIGS. 2A-B are top views, depicting one embodiment of a scissor device.
Figure 2B:
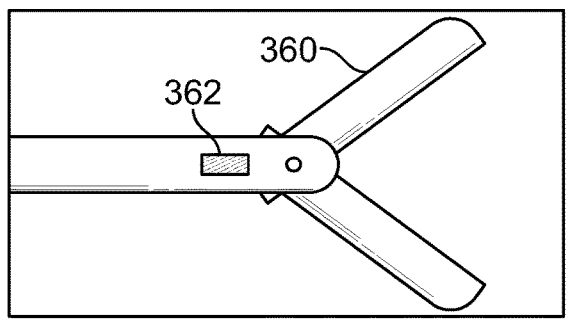

With respect to FIGS. 2A-B, there are shown blunt tipped scissors 360 that are configured at a distal end portion of a cellulite treatment assembly 220. The blunt tipped scissors 360 are advanced under the skin to a target and used to engage suspected septa. As in each of the disclosed approaches and apparatus, should engagement of such septa result in some change in the dimple or depression expressed on the skin, the treatment structure, here scissors 360, are manipulated to disrupt, cut or slice the septa. Thus, the scissors 360 are opened and septa is placed between its blades. Next, the blades are advanced against or caused to be closed about the septa to thereby cut, slice or sever the septa, thus relieving the tension between tissue layers and eliminating or minimizing the appearance of the dimple or depression expression on the skin. Actuation of the scissors is accomplished from a proximal end of the treatment device such as by pulling a wire or advancing and pushing an elongate member associated with the scissor arrangement (not shown). Illumination can be provided by a light 362 configured proximal of the scissors 360 so that transillumination can be employed to track the location of the distal portion of the treatment assembly 220. Additionally, or alternatively, in each disclosed embodiment, illumination can be via a lightguide from an external light source or via one or more LEDs. Illumination aids the user both with locating the treatment device as well as proper depth placement as transillumination decreases with increasing tool depth. In one aspect, the amount of illumination is set to ensure proper depth of a treatment device or structure, the level of illumination targeted being adjusted for skin type, thickness, presence of fat and pigment. Once selected or targeted septa are cut, sliced or disrupted, in each of the disclosed approaches, the cellulite treatment device can be or is advanced or repositioned to treat additional target areas from the same or different skin insertion device.

Figure 3A:
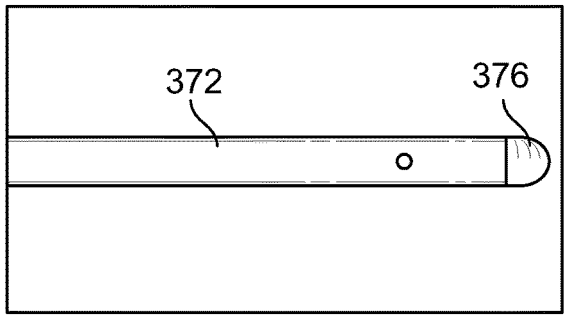
FIGS. 3A-E are top views, depicting embodiments of hook and v-structure for treating cellulite.
Figure 3B:
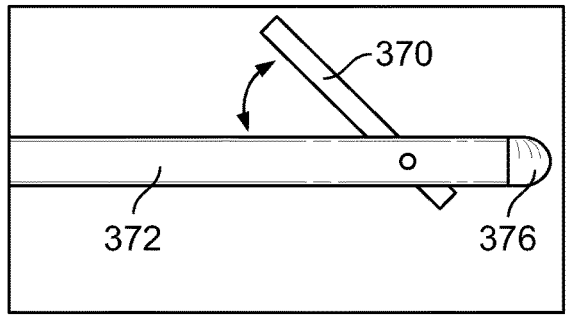
Figure 3C:
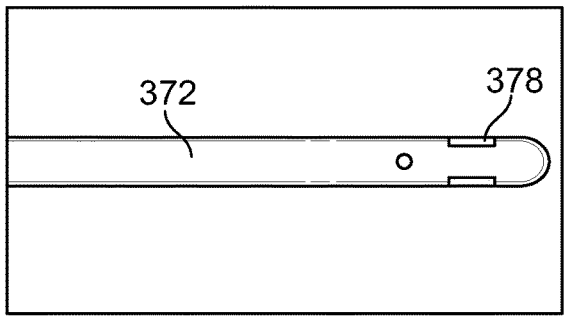
Figure 3D:
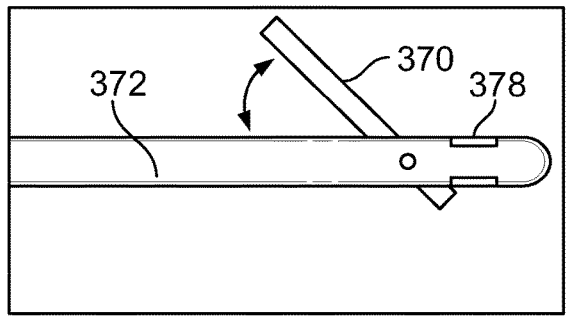
Figure 3E:
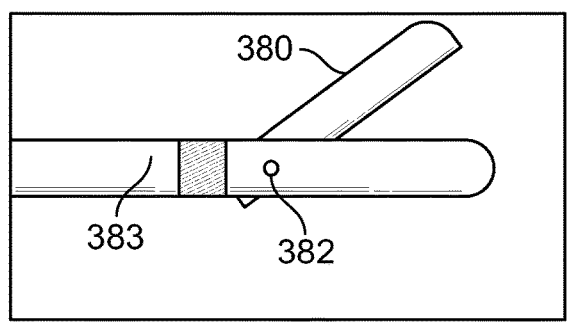

Various approaches to laterally projectable tissue engaging and/or cutting structure are shown in FIGS. 3A-E. The distal end portion of the cellulite treatment assembly can embody a side opening hook arm 370 that rotates with respect to a longitudinal shaft 372 to alternatively display septa engaging and/or septa cutting structure (FIGS. 3A-B). The hook arm 370 is configured to swing out from a proximally directed, longitudinal configuration where it is parallel with the shaft 372 to a laterally projected configuration to thereby capture and tension septa once the device is advanced beyond the target location and then retracted. Here again, so engaging septa can confirm that the septa responsible for creating skin surface dimples or depressions is being targeted as such engagement with septa will be reflected in a physical change of the skin surface. Disruption results from tensioning septa against a narrow edge of the hook arm 370 or against a cutting or sharpened edge thereof. An outward facing portion of the arm 370 can define blunt structure and a cutting edge can be positioned within the acute angle defined by the arm 370. With this structure, increased tension can be employed to cooperate with a limited cutting edge as septa is drawn within the acute angle defined by the arm 370. In FIGS. 3A-B, transillumination functionality is provided by a light 376 configured at a terminal end of the device, whereas in the assembly shown in FIGS. 3C-D, slits 378 formed in the shaft proximal the terminal end allow for the dispersion of light energy. In FIG. 3E, cutting and septa engaging structure is embodied in a single moving arm 380, while illumination is provided proximal a hinge 382, but the same can be positioned at the terminal end of the device. As in the previous embodiments, the exposed edges of the arm 380 can be blunt or sharp for cutting or slicing. Also, here, the arm 380 assumes a distally directed, longitudinal configuration parallel to the shaft 372 for advancement between tissue layers, and the arm 380 is caused to be projected laterally outwardly to both capture and cut or slice target septa. Actuation of the engaging and cutting structures can be accomplished through the manipulation of a proximally positioned lever or trigger connected to the same via a wire or longitudinally directed shaft (not shown). Once a desired area is treated, additional target areas can be addressed.

Figure 4A:
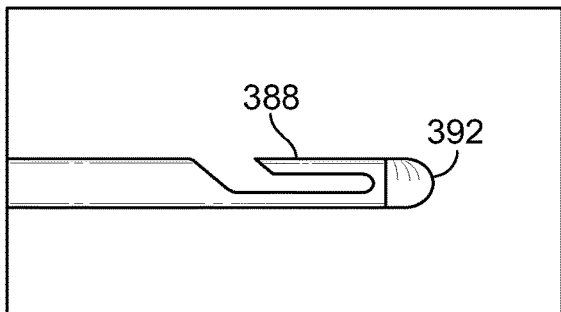
FIGS. 4A-B are top views, depicting treatment structure involving a hook treatment structure.
Figure 4B:
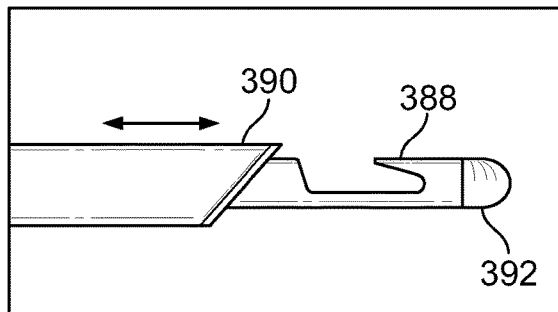

The distal end portion of the cellulite treatment assembly 220 can alternatively or additionally embody an internal static hook 388 (FIG. 4A) to treat target areas from one or more skin insertion sites. A terminal end of the assembly or the hook itself 388 can be employed to be placed about tissue and to engage and test tissue to identify target septa. Sharpened edges within the hook can be used to engage and cut septa that has been targeted and identified as being associated with the expression of cellulite on the skin. As shown in FIG. 4B, a concentric sliding tube 390 actuatable from a proximal end of the cellulite treatment assembly can additionally be provided to be moved proximally and distally with respect to a hook 392. The tube 390 can include selectively sharpened edges or can be blunt to thus cooperate with the hook 392 to capture, cut, slice, tear or disrupt septa. The assembly can further be advanced in a spinning manner to cut or slice through septa. Employing the tube 390 to cut tissue results in a section being taken out of the septa as spaced cuts are simultaneous made through the septa.

Figure 5A:
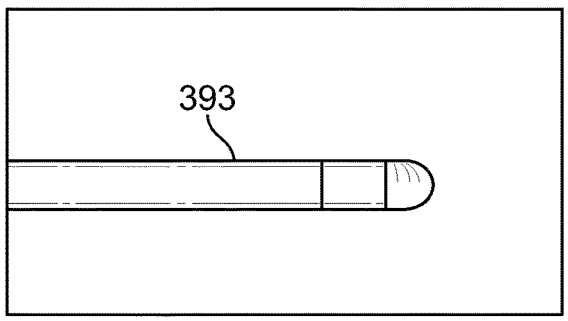
FIGS. 5A-C are top views, depicting hook and slide approach to treatment structure.
Figure 5B:
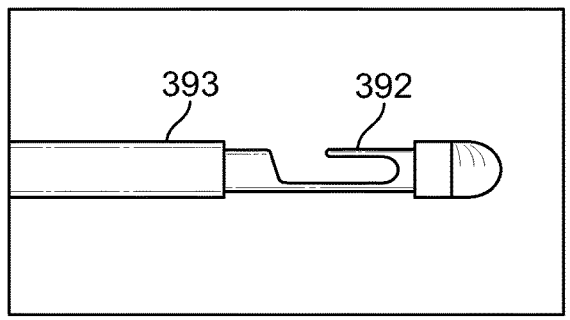
Figure 5C:
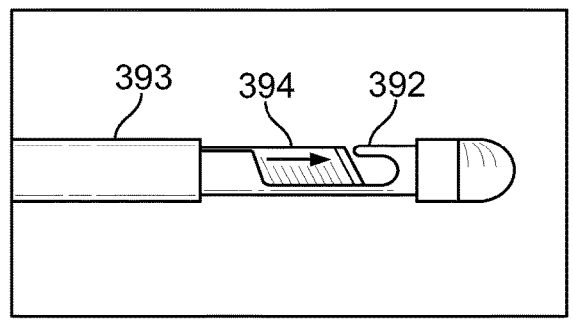

As shown in FIGS. 5A-C, in a related approach to treating multiple treatment sites, a cutting, slicing or disrupting assembly additionally or alternatively includes a longitudinally extendable and retractable sheath 393 that alternatively covers and exposes a hook 392, and further embodies an extendable and retractable guillotine-like blade 394. The blade 394 is sized and shaped to slide within an opening defined by the hook 392 and to cut tissues snared by the hook 392. Thus, in its distal position, the sheath 393 facilitates the assembly to define structure suited for advancement to a treatment site. Withdrawing the sheath 393 through manipulation of structure connected thereto positioned at a proximal end of the assembly, exposes the hook structure 392. The hook 392 is used to engage and capture target tissue to test if the targeted tissue is associated with the expression of cellulite on the skin. While the hook maintains the septa in a captured position, the guillotine blade 394 is advanced through manipulation of a proximally positioned actuator (not shown) to slice or cut captured septa to thereby eliminate or minimize the appearance of cellulite.

Figure 6A:
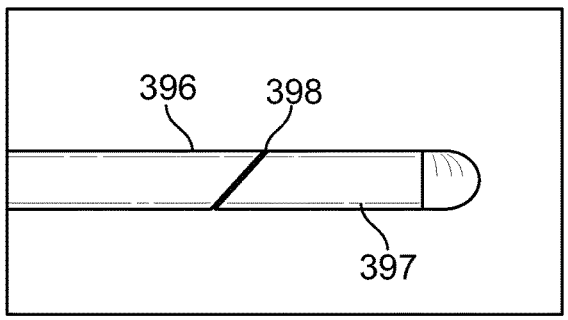
FIGS. 6A-B are top views, depicting segmented treatment structure.
Figure 6B:
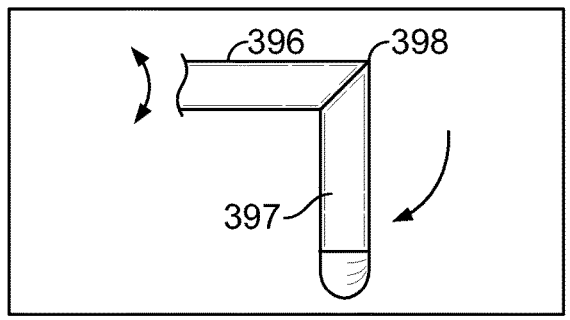

Turning now to FIGS. 6A-B, there is shown yet another approach to a distal end portion of a cellulite treatment system 220. Here, a two-segment hook assembly 396, 397 is held together with a tensioning force (such as a spring or a wire or shaft connected thereto) on angled surfaces 398. When one segment is turned relative to the other, an angle is formed between the two segments. It is to be recognized that the length of this hooked structure can be adjusted to fit a particular need. Further, selected edges of the hook assembly can be sharpened or be blunt. In one particular aspect that applies to each of the disclosed embodiments, the hook can be covered in an elastomer such that as the elastomer is tensioned, the elastomer is displaced thus exposing the sharpened edges. When untensioned, the sharpened edges are safely encased. In another approach, a spring-loaded shield can replace the elastomer. Manipulation of the two-segment hook assembly 396, 397 within tissue and between tissue layers allows for both the engagement and identification of target septa as described herein, as well as the slicing, cutting or disruption of targeted septa.

Referring now to FIGS. 7A-D, a cutting, slicing or disrupting treatment assembly is defined by a projecting linkage arrangement. A first link 400 includes a blade 401 and is rotatably attached at one end to a second link 402. The opposite end of the first link 400 slides with respect to a longitudinal shaft 405. A second end of the second link 402 is rotationally affixed to a distal point on the shaft 405. In one embodiment, as a drive shaft 407 attached to the opposite end of the first link 400 is advanced, the links 400, 402 fully overlap (FIG. 7C) to create a hook arrangement sized and shaped to engage tissues and to test septa to determine if such septa is associated with the expression of cellulite on a patient's skin. In this arrangement, the blade structure 401 is not exposed, but rather it is protected or covered by the second link 402. When cutting or slicing action is desired, such as once selected septa are targeted, the drive shaft 407 is slightly retracted, thereby exposing the blade structure 401 to thereby present a sharp edge for cutting of hooked septa (See FIG. 7D). To store the links 400, 402 away for advancement or repositioning between tissue layers, the shaft 407 is withdrawn completely which results in the links 400, 402 assuming a co-linear and parallel relationship with the shaft.

Figure 7A:
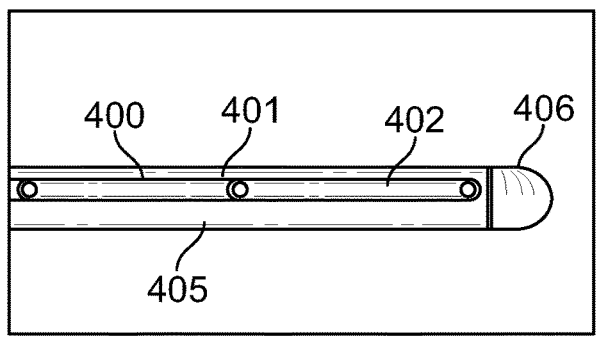
FIGS. 7A-N are top and partial cross-sectional views, depicting a treatment device with linkage hooking and cutting structure.
Figure 7B:
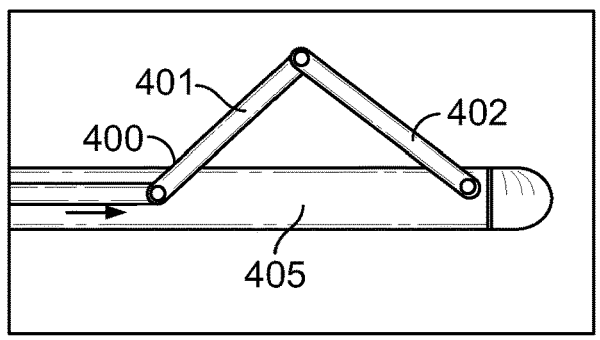
FIGS. 7O-P are isometric views, depicting one embodiment of a treatment system and a treatment device.
FIG. 7Q-X are top and partial cross-sectional views, depicting further features of a treatment device.
Figure 7C:
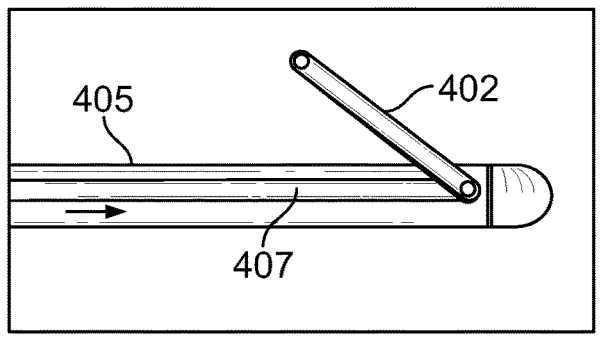
Figure 7D:
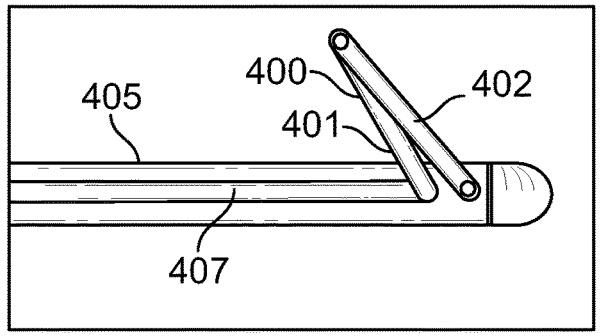
Figure 7E:
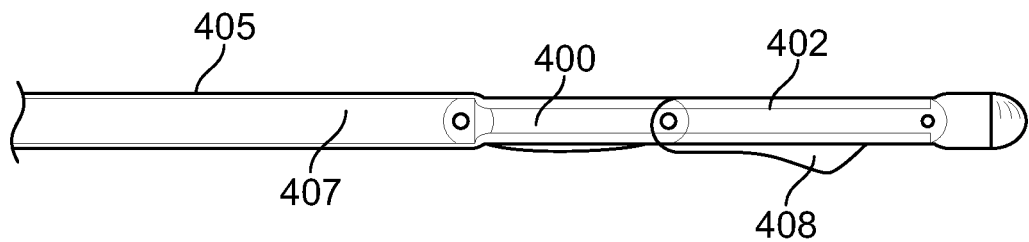
Figure 7F:
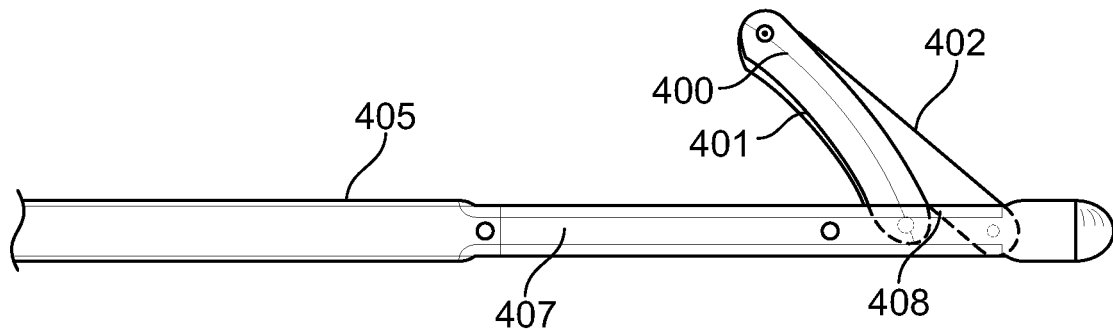
Figure 7G:
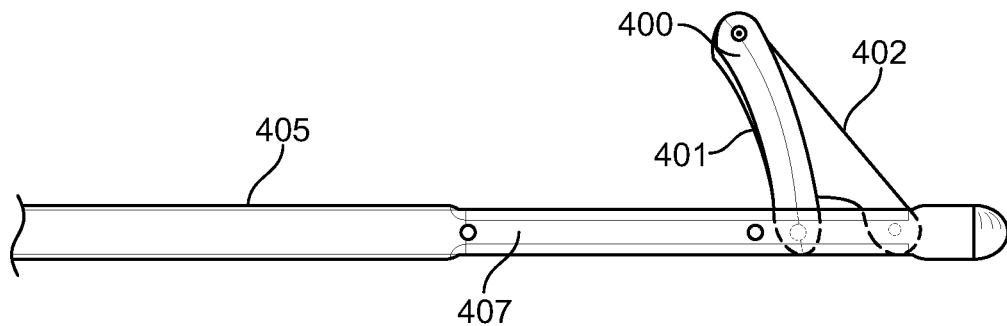
Figure 7H:
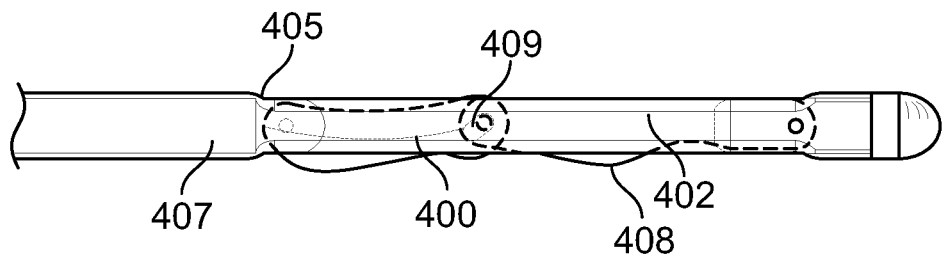
Figure 7I:
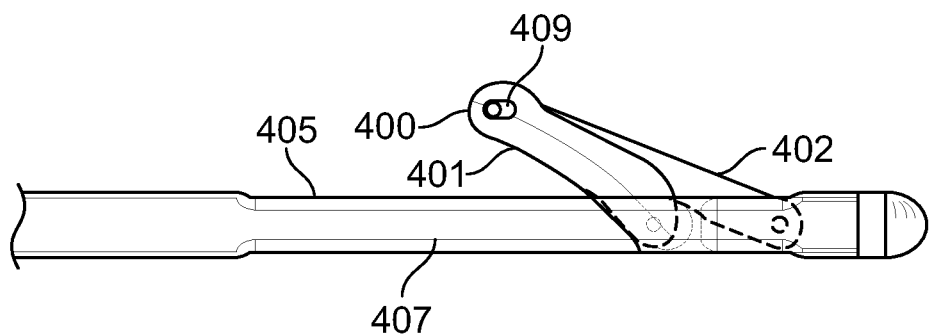
Figure 7J:
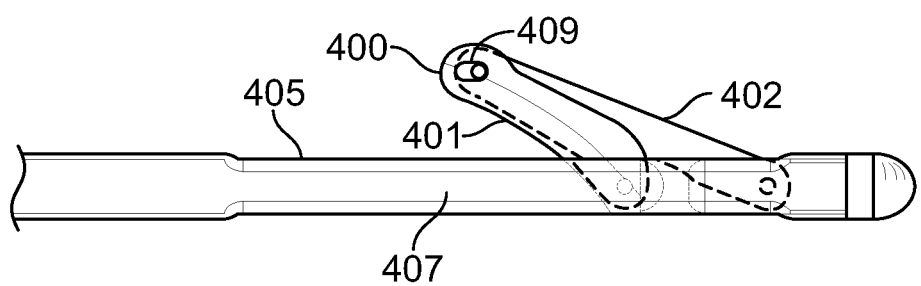
Figure 7K:
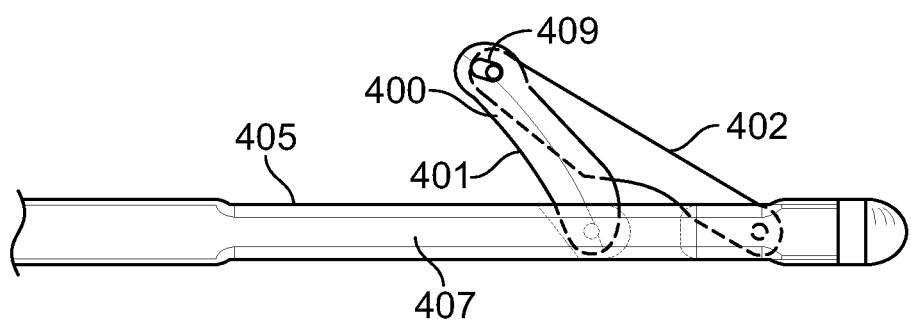
Figure 7L:
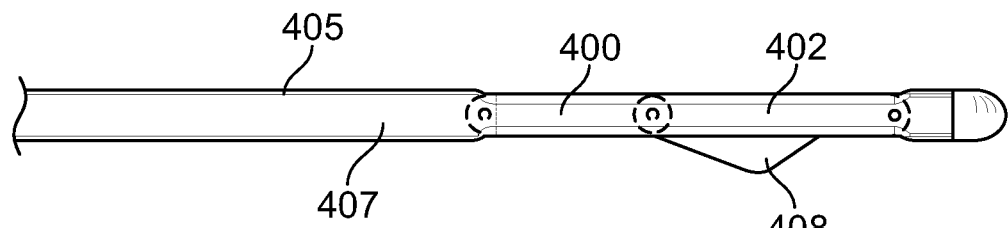
Figure 7M:
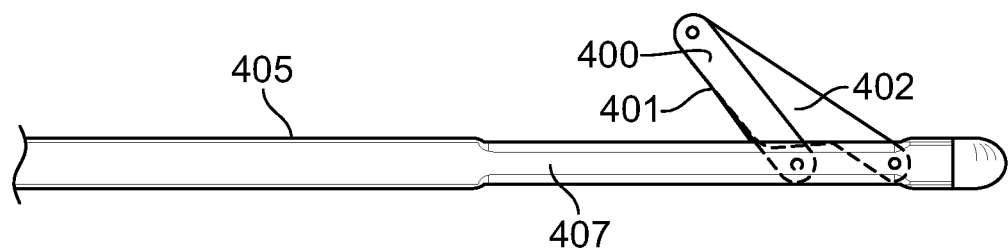
Figure 7N:
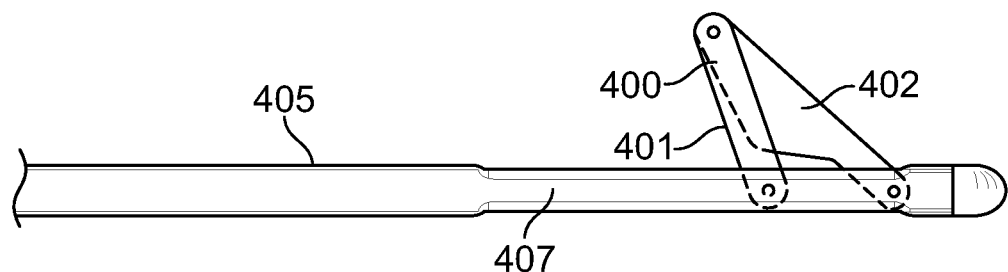

In a related approach, as shown in FIGS. 7E-G, the first link 400 defines a curved blade that is rotatably connected to a second link 402 that includes a generally triangular or pointed projection 408 that is sized and shaped to cover the blade 401 when the assembly is placed in a hooking configuration (See FIG. 7F). When the drive shaft 407 (shown in phantom lines) is manipulated such that the blade 401 is exposed (See FIG. 7G), the blade 401 can be employed to cut septa. When advancing the treatment device to and between interventional sites, the drive shaft 407 is withdrawn so that the assembly defines a lower profile where the first 400 and second links 402 are generally longitudinally aligned (FIG. 7E). As shown in FIGS. 7H-K, the rotatable connection between the first 400 and second links 402 can additionally or alternatively be characterized by a slotted arrangement 409. With such a connection, the projection 408 can be smaller, thus resulting in the overall profile of the treatment device being smaller. Notably, in a septa hooking configuration (FIG. 7J) after pulling the drive shaft 407 proximally slightly, an end of the first link 400 resides in a proximal position within the slot 409 and the smaller projection 408 of the second link 402 overlays the blade 401. In a septa cutting configuration (FIG. 7K), the end of the first link 400 assumes a distal position within the slot 409 such that the blade 401 is exposed for cutting. With reference to FIGS. 7L-N, in another embodiment, the first link 400 can also define a straight blade 401. In this approach, the projection 408 is larger to therefore provide necessary coverage of the blade 401 when the device is placed in a hooking configuration (FIG. 7M). Each of the foregoing devices can also additionally or alternatively include other of the features disclosed herein such as structure providing transillumination and radiofrequency cutting and coagulation.

Figure 7O:
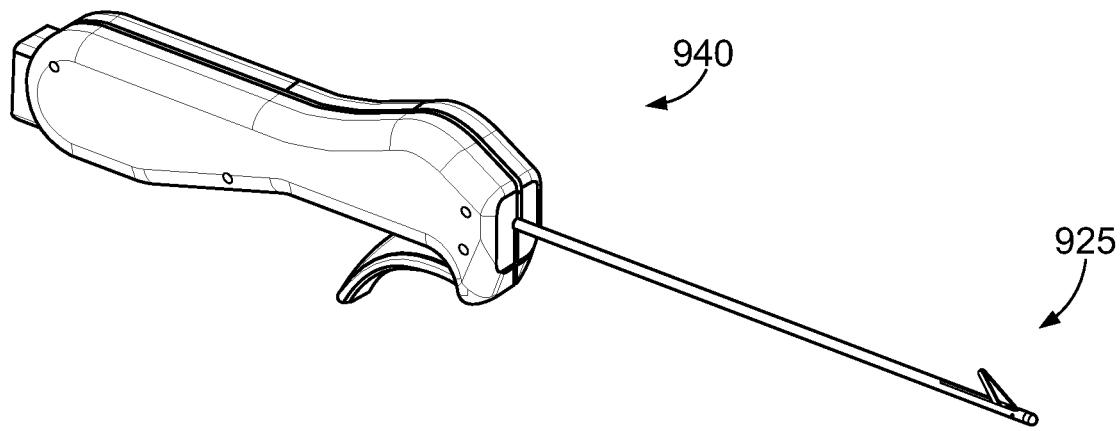
Figure 7P:
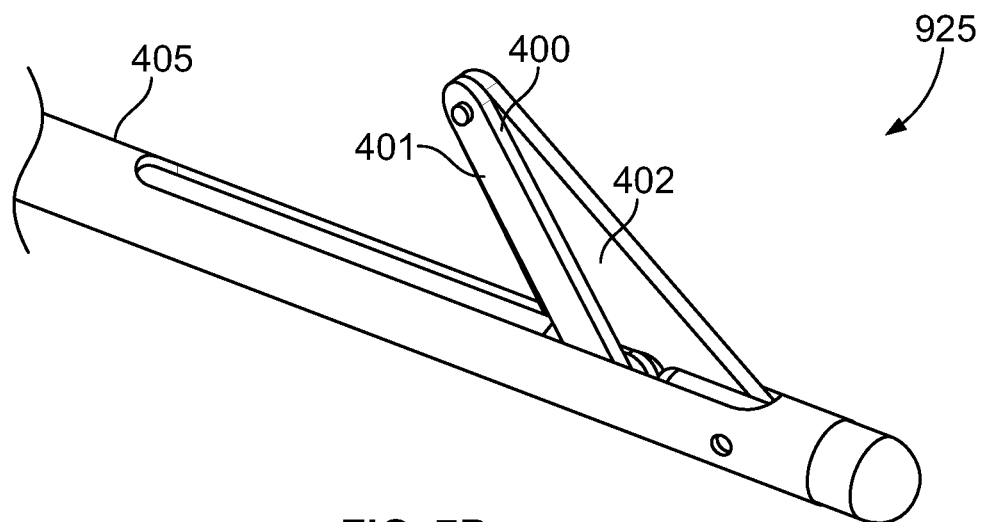

Referring to FIGS. 7O-P, there is shown one embodiment of a cellulite treatment system 940 (described in more detail in connection with FIG. 11) that can be employed to treat cellulite. As shown (FIG. 7O), a distal end portion of the treatment system 940 is configured with a treatment device 925. Here, the treatment device of FIGS. 7L-N is shown positioned at the distal end of the treatment device 940 in a hooking configuration (FIG. 7P). Any of the disclosed treatment devices can be so configured at the distal end of the treatment system 940.

Figure 7Q:
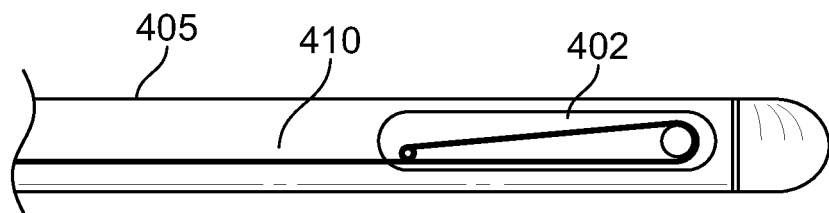
Figure 7R:
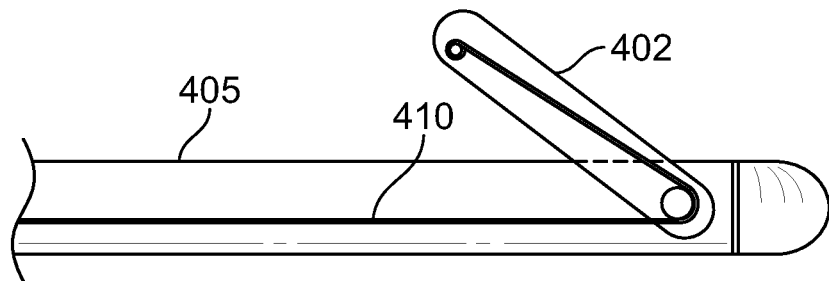
Figure 7S:
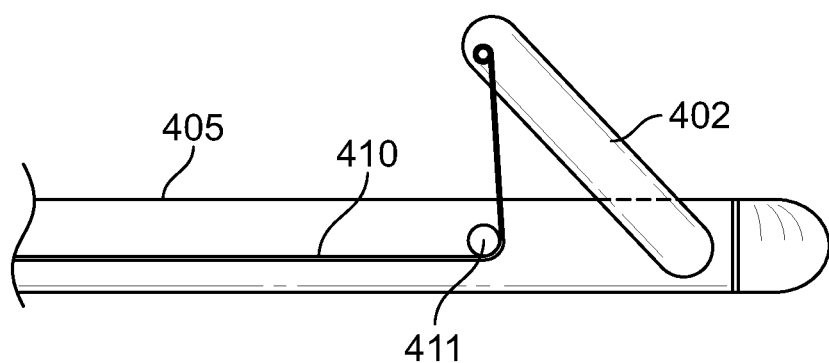

As shown in FIGS. 7Q-S, the treatment device can alternatively or additionally include a wire 410 that is rotatably attached to the second link 402. Here, a proximal portion of the wire 410 serves as structure that can be advanced and retracted to configure the treatment device into closed, hooking and cutting positions. Further, the wire 410 is formed into a coil 411 (See FIG. 7S) that provides necessary strength and robustness for moving the wire 410 between closed (FIG. 7Q) and cutting (FIG. 7S) configurations. In a septa hooking configuration (FIG. 7R), the second link 402 covers the wire 410 thereby prohibiting the wire to be exposed to target septa, and the coil 411 aligns with the second blade 402. In its closed configuration (FIG. 7Q), the treatment device defines a low profile suited for being advanced to and between treatment targets. The proximally facing edge of the wire can be sharpened to produce a cutting edge. In addition, or alternatively, the wire can be an electrode attached to a radiofrequency generator so that the wire can be used for electrocautery or RF cutting of target tissue.

In other alternative or additional aspects, the elongate member 224 of a cellulite treatment device, as shown in FIGS. 7T-U, can embody a tubular shape, including a lumen 412 extending therethrough, the lumen providing a space for a light fiber 414. Notably, the remaining space not occupied by the light fiber 414 defines a crescent moon shape from a cross-sectional view perspective. In one approach, the tubular portion terminates at the treatment device 225.

As shown in FIGS. 7V-X, again in one or more embodiments, the lumen 412 of the elongate member 224 can be sized and shaped to individually receive one or more additional septa engaging, cutting, slicing or disrupting treatments devices 225 or for the injection of anesthetic, medications or other substances such as fillers or fat transfers before, during or after treatment. In one approach, a treatment site can be dosed or filled with material contemporary with or during a treatment procedure rather than using a separate device and procedure to accomplish the same. Notably, each of the disclosed embodiments can be combined to provide a combination cellulite treatment assembly in a similar manner.

Figure 8A:
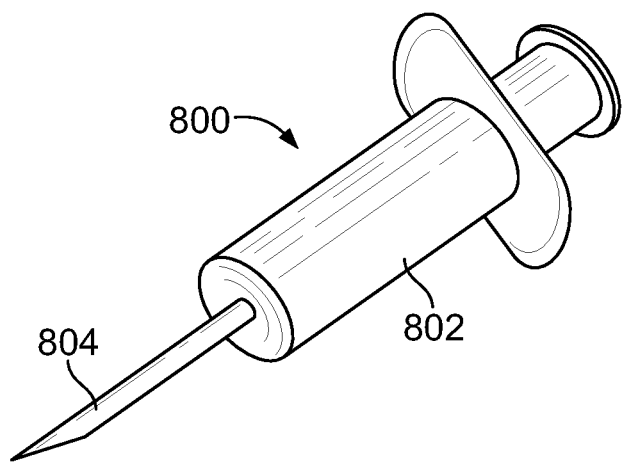
FIGS. 8A-C are perspective views, depicting components of a spot treatment system.
Figure 8B:
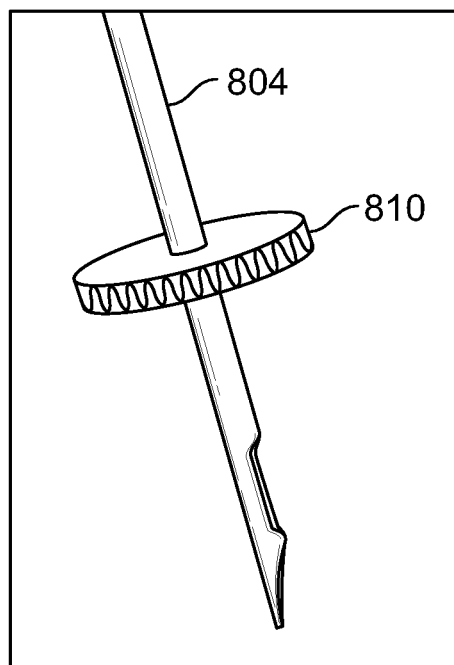
Figure 8C:
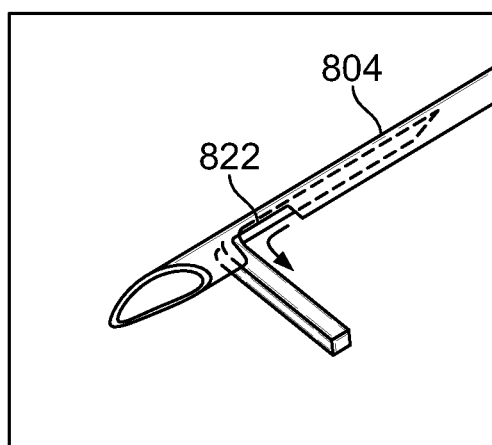

In an alternative embodiment, spot treatment of septa is possible employing a cellulite treatment system 800 configured to address one interventional site at a time. Thus, cutting structures can be inserted perpendicular to skin to accomplish treatment or can be advanced below the skin in a direction generally parallel to the surface of the skin or angles with respect thereto. Moreover, the structures of each of the disclosed tissue engaging and cutting devices can alternatively or additionally be configured to be used for treatment. In one particular aspect, the cutting action is rotary in character, such that cutter structure spins with controlled speeds configured to cut septa in a manner dictated by observed septa structure at the interventional site. The cutter is alternatively or additionally configured to accomplish cutting action by engaging or dragging the cutter against target septa. Again, here, the degree to which the dragging is performed is dictated by the septa and septa inherent structure. In one approach, a system 800 includes an elongate handle 802 that is provided for grasping by an operator (See FIGS. 8A-C). Extending longitudinally from the handle 802 is a needle assembly 804. The needle 804 is configured to create an insertion site adjacent a specific cellulite target area, or directly into a dimple cellulite site. Further, it is through the needle assembly 804 that interventional site instrumentation is advanced to address and treat septa residing below a dimple expression on a subject's skin. Additionally, in one embodiment, a dilator can include or cooperate with a harmonic scalpel, selective cautery structure or energy transmitting structure for dissecting tissue and/or controlling bleeding. In one approach, once a correct depth is accessed, a cutting instrument is swept 360 degrees to cut surrounding septa. Additionally or alternatively, an endoscope can be employed in an assembly including a cutter to sever septa in a targeted manner. That is, septa that are viewed by the endoscope are targeted for severing by the cutter. Here, direct visual confirmation of a treatment is provided.

In one embodiment, the needle 804 can be fashioned with a stop 810 that is positionable along the needle 804 as desired or dictated by a particular procedure or anatomy. The stop 810 is located so that when the needle 804 is placed within tissue, its terminal end is positioned at a desired depth such as between tissue layers connected by septa. A side opening 822 is further provided at the terminal end of the needle 804. It is through this side opening 822 that interventional devices such as cutters, scalpels, cautery structure or energy transmitting devices are advanced between tissue layers. Such devices are then employed to selectively treat the septa residing below the skin for the purpose of eliminating or reducing the appearance of cellulite. Once it is determined that the treatment has been successful, the spot cellulite treatment system 800 is then removed and employed at another location exhibiting cellulite.

Figure 8D:
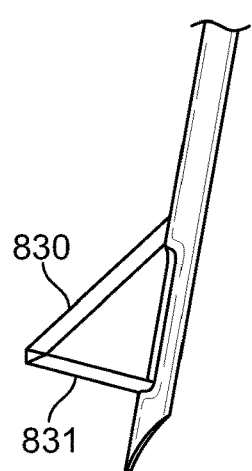
FIGS. 8D-K are side views, depicting additional approaches to treatment structure.
Figure 8E:
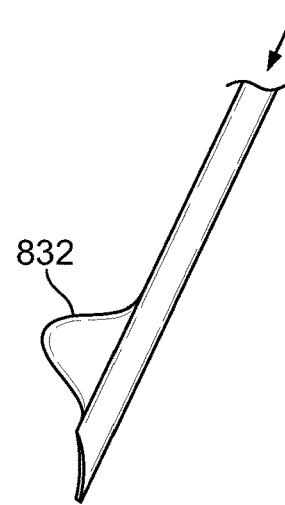

Turning now to FIGS. 8D-J, there are shown further aspects of tools employed for treatment of cellulite in alternative approaches. Such structure can also be employed as distal end structure for the cellulite treatment assembly shown in FIG. 1D. With reference now to FIG. 8D, a treatment device can be equipped with a wire that includes linkages 830 manipulation of which function to push out a cutting blade 831 arrangement that is sized and shaped to cut connective tissue. As shown in FIG. 8E, a distal end portion of a spot treatment device can be equipped with a wire arranged to be advanceable to define a loop 832, the loop having a gauge facilitating the structure to be employed to cut tissue. Alternatively, RF energy can be employed to cut septa.

Figure 8F:
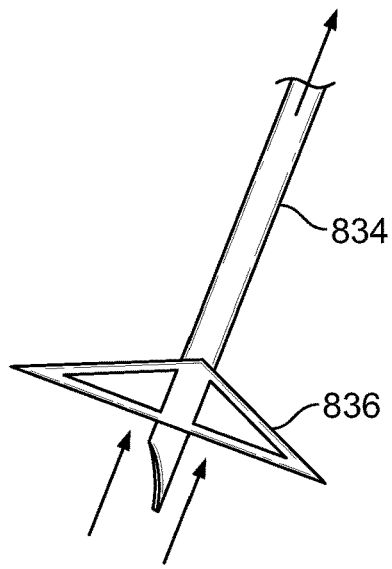
Figure 8G:
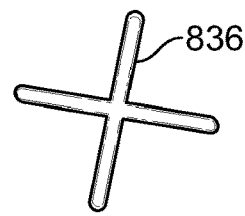
Figure 8H:
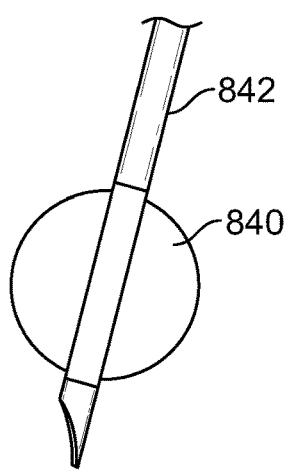
Figure 8I:
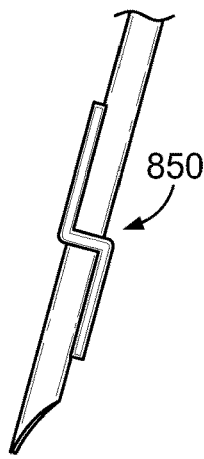
Figure 8J:
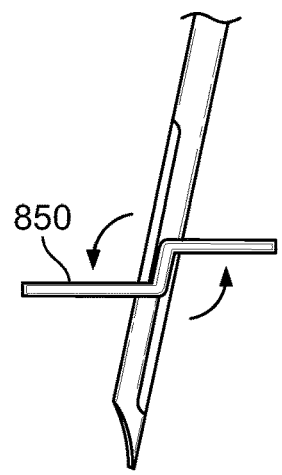

FIGS. 8F-G depicts a deformable hypotube 834 that is expandable such that two or more arms 836 project to define blades for cutting in another non-atraumatic approach to treatment. FIG. 8H illustrates a balloon structure 840 attached to a needle hypotube 842 which can be expanded below a dimple to eliminate or reduce the appearance of cellulite. Finally, in another non-atraumatic approach (FIG. 8I-J), a distal end portion of a spot treatment device can be fashioned with blades 850, one to cut for deployment and at least one that is configured to rotate and cut connective tissue.

Figure 8K:
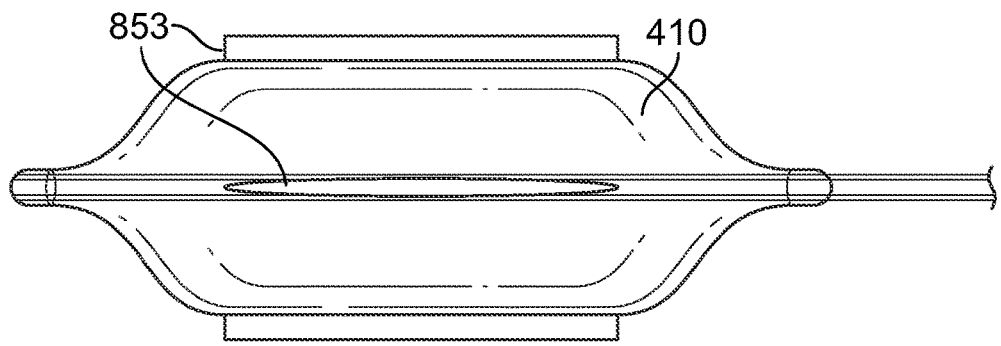
Figure 8L:
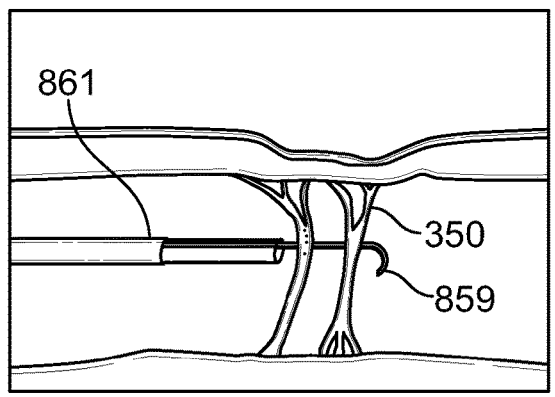
FIGS. 8L-V are cross-sectional views, depicting various treatment approaches involving a lasso.
Figure 8M:
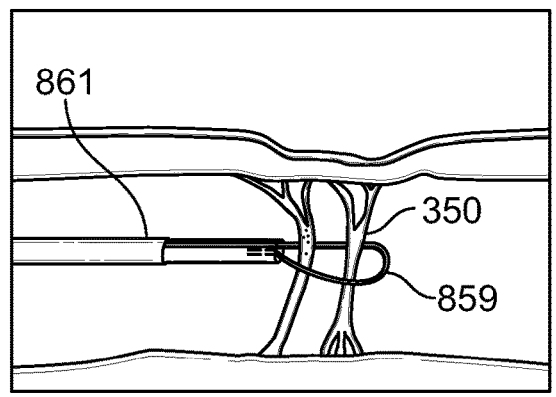
Figure 8N:
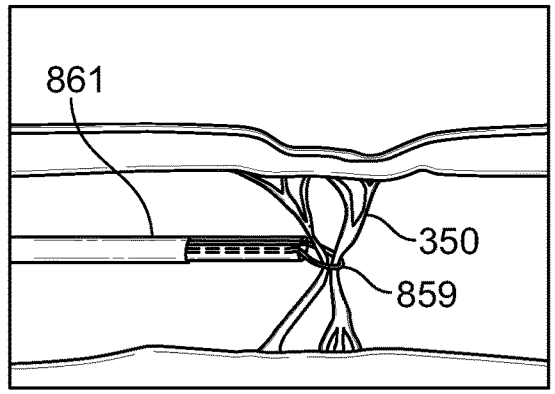
Figure 8O:
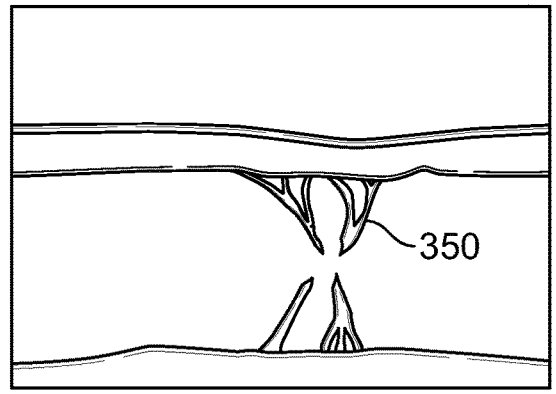
Figure 8P:
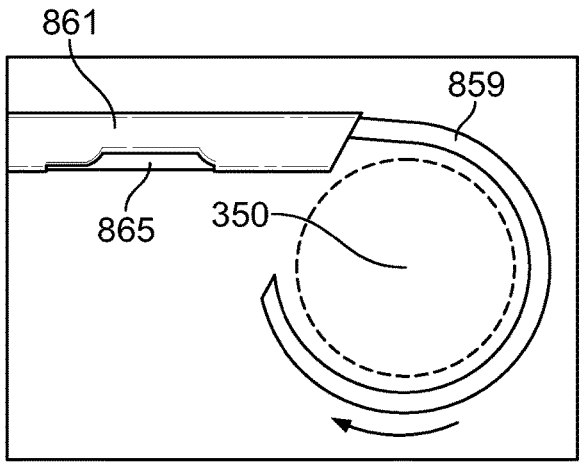

As shown in FIG. 8K, a dilator 410 can form a distal end portion of a cellulite treatment device and additionally be equipped with longitudinally extending blades 853 that are deployed when the dilator 410 is expanded. The blades 853 are configured to engage and cut target tissue or septa in an alternative approach to treatment. Such cutting is employed in an alternative to a non-traumatic approach and accomplished by rotating or otherwise advancing, sweeping or retracting the dilator 410. The assembly is unexpanded and withdrawn from the interventional site after use such as through a tube.

In yet another treatment approach, a curved wire forming a lasso 859 and forming a distal end portion of a cellulite treatment assembly and being advanceable and retractable through a shaft 861 (FIGS. 8L-O) can be deployed about septa 350 within a target zone. Pulling the lasso 859 to reduce the perimeter it defines results in cutting septa 350 and treating cellulite. In one aspect, the lasso is formed from nitinol wire, or is pre-formed wire or pieces thereof. The lasso 859 encircles targeted septa and via tightening, cuts the septa. One approach involves cutting a targeted area without shaft movement thus providing a controlled approach to treatment.

Figure 8Q:
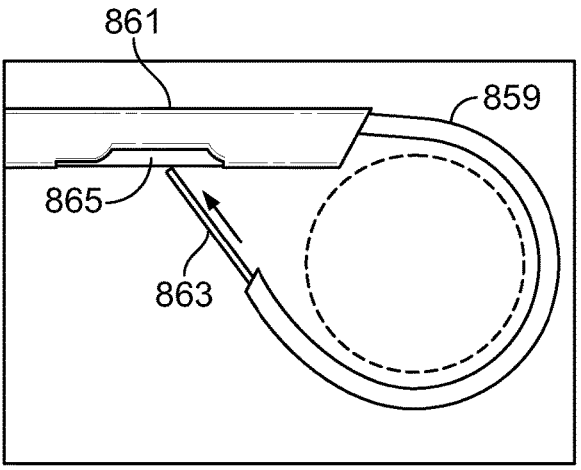
Figure 8R:
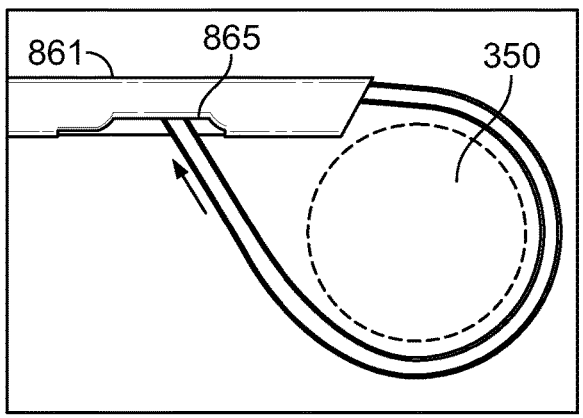
Figure 8S:
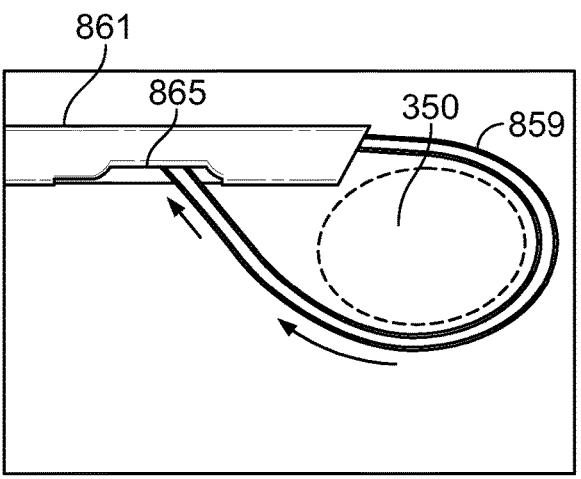
Figure 8T:
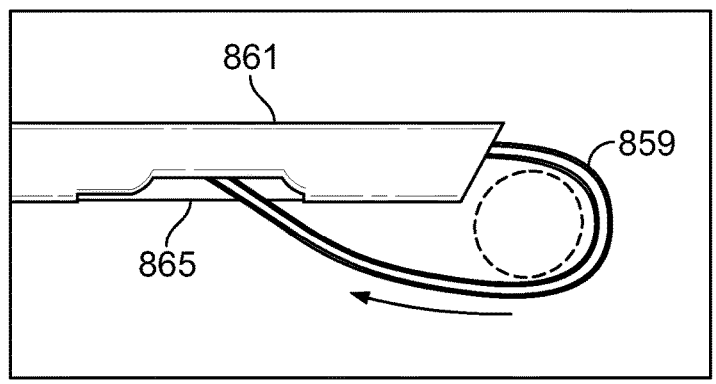

As shown in FIGS. 8P-T, the lasso 859 can additionally or alternatively define a tube and the assembly can additionally include a wire 863 that is slidably configured within the tubular structure. After septa 350 is targeted, the lasso structure 859 is partially configured about the septa 350 by pushing it out of shaft 861. The wire 863 is then advanced within the lasso 859 and out of a terminal end of the lasso 859 (FIG. 8Q). The wire 863 is then advanced toward a slot or opening 865 formed in the shaft 861 and is retained therein. Thereafter, the lasso 859 is further advanced to and into engagement with the shaft 861 to thereby define a completed hoop or loop (FIG. 8R). The lasso 859 is then pulled tight about the target septa 350 to cut, slice or disrupt the septa as desired (FIG. 8T). Alternatively, the completed hoop can remain in its larger hooped configuration and the entire device can be pulled proximally to slice or disrupt the encircled septa. After treating the target tissue, the lasso 859 and wire 863 are pulled proximally through the shaft 861 so that they disengage from the slot 865 and are withdrawn completely or partially within the shaft 861 so that the treatment device can be used in additional locations.

Figure 8U:
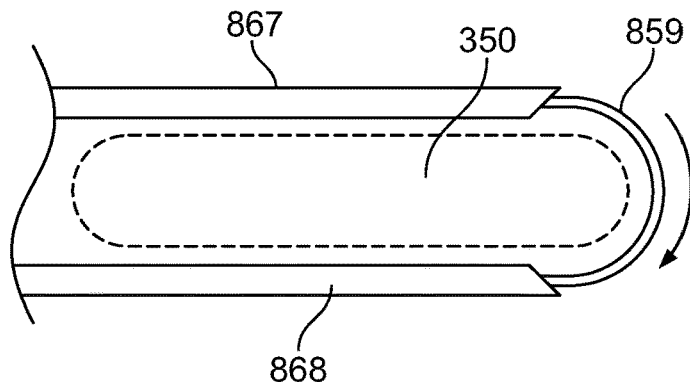
Figure 8V:
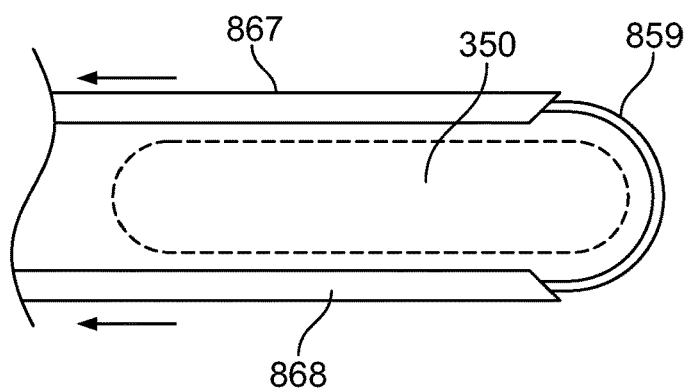

In a related lasso treatment approach (FIGS. 8U-V), there are provided a pair of elongate tubes 867, 868 configurable in a generally parallel arrangement about target septa 350. The lasso 859 is advanced within the first tube 867 and out a terminal end thereof and toward the second tube 868 (FIG. 8U). The lasso 859 is then captured by the second tube 868 so that the treatment device encircles target septa 350. The assembly is then pulled proximally to cut, slice or disrupt target tissue. After treatment, the lasso 859 is withdrawn within the first tube 867 and released from engagement with the second tube 868. The assembly is then positioned as necessary to treat additional areas.

Figure 9A:
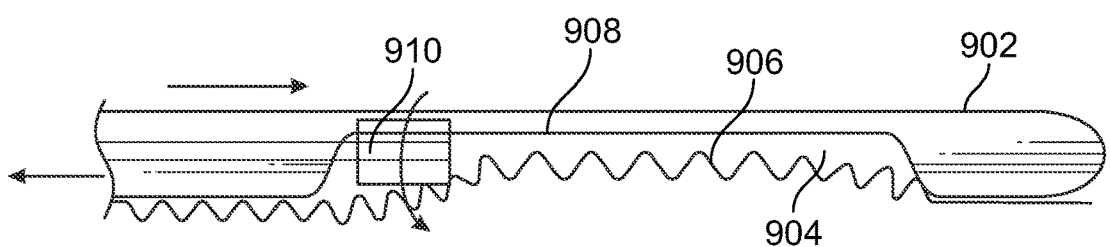
FIG. 9A-B are cross-sectional views, depicting an atherectomy-type device and use thereof.
Figure 9B:
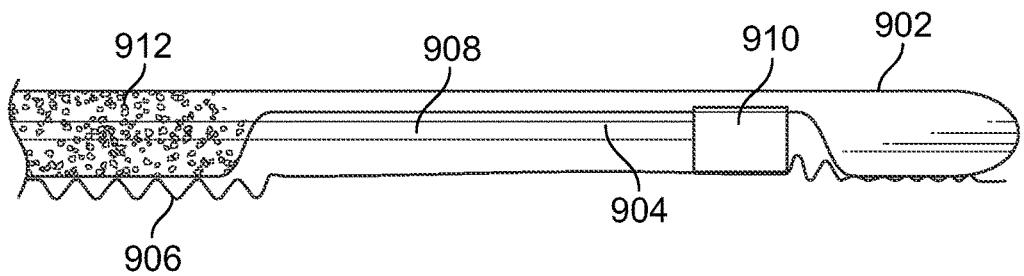

An atherectomy-style cutter 902 (See FIGS. 9A-B) also can be alternatively or additionally configured to remove tissue through an opening 904 on the side of the instrument, can be used in certain ancillary, more traumatic approaches to treatment. Cutting structure 906 is attached to an elongate actuator 908 via a block or other connection 910. Manipulation of the actuator 908 causes the cutting structure 906 to engage targeted tissue. A lumen 912 is further provided as a conduit for applying a suction force to the interventional site so that severed or macerated tissue 912 can be removed. This device can be employed to harvest fat for subsequent placement at a site that has been treated with a dilator and used to fill the space created. The cutter 902 can also be employed as a primary treatment device for cutting septa to treat cellulite.

Figure 10A:
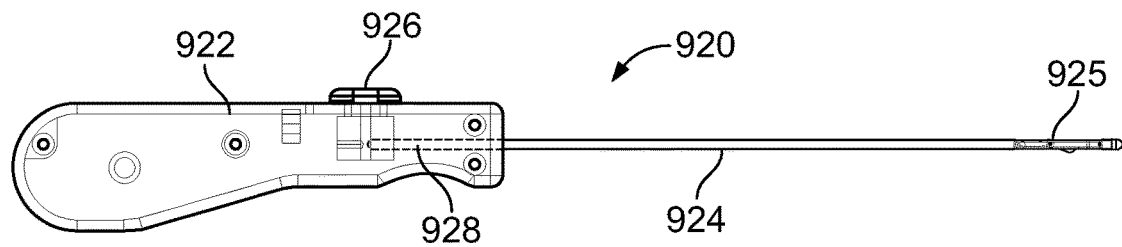
FIG. 10A-C are side views, depicting components of another treatment system.
Figure 10B:
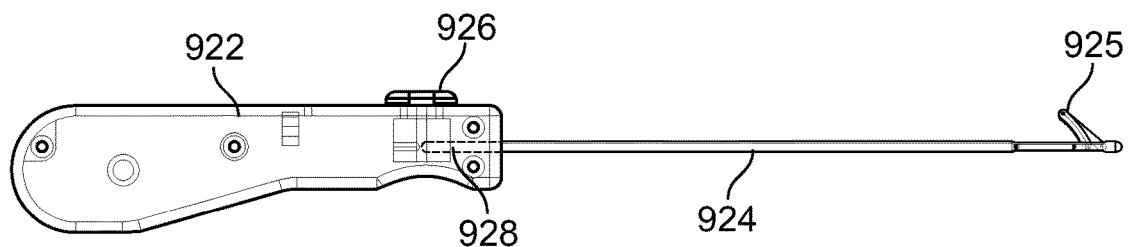
Figure 10C:
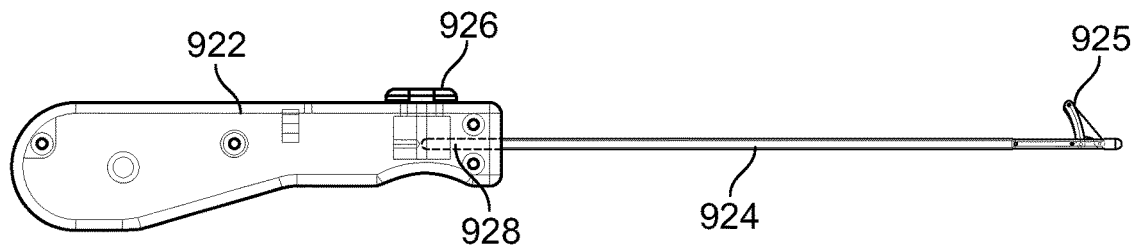

Turning now to FIGS. 10A-C, there is shown one preferred embodiment of a treatment system 920 that can be used in connection with one or more of the previously described devices for treating target tissue. The treatment system 920 includes a handle 922 and an elongate member 924 extending longitudinally from the handle 922. As described above, a force gauge or sensor (electronic or mechanical) can be provided to ensure that a pre-determined amount of force would be applied to the tissue when testing the septa to prevent over or under pulling. Moreover, a treatment device 925 capable of one or more of engaging, slicing, cutting or disrupting connective tissue is configured at a distal end portion of the elongate member 924. Thus, any one or more of the treatment devices described herein can define the treatment device 925. All cutting means can be combined with or further energized with RF, a laser, ultrasonic or thermal energy to produce cutting and coagulation together or separately.

The handle 922 is equipped with a button or sliding trigger 926 that is configured to slide along a top surface of the handle 922. The trigger 926 is attached to a proximal end portion of a shaft or wire 928, a distal end portion of which is associated with or attached to the treatment device 925. In a closed configuration, the trigger 926 is positioned in its most proximal position (FIG. 10A), and the treatment device 925 maintains a generally longitudinally aligned configuration. As so configured, the treatment system 920 can be positioned or re-positioned to accomplish desired cellulite treatments. Moving the trigger 926 to its most distal position in turn causes the shaft or wire 928 to advance distally and place the treatment device 925, for example, in a configuration for hooking target tissue (FIG. 10B). Withdrawing the trigger 926 to an intermediate position, exposes a cutting structure (such as a blade or cutting wire) to thereby configure the treatment device 925 for cutting, slicing or disrupting target tissue (FIG. 10C). Detents or other cooperating structure can be incorporated into the handle or trigger to secure the trigger in one or more positions as well as to provide a tactile feedback regarding positioning. Further, the system 925 can alternatively or additionally include any of the previously described functionality such as structure for providing transillumination and radiofrequency cutting and coagulation.

Figure 11:
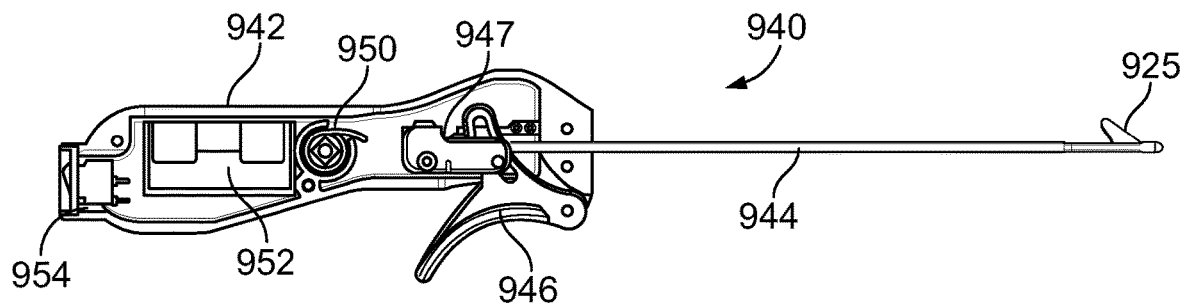
FIG. 11 is a side view, depicting components of yet another treatment system.

As shown in FIG. 11, in another embodiment, the treatment system 940 includes a handle 942 and an elongate member 944 extending from the handle. A shaft or wire (not shown) configured within the elongate member 944 is attached to a treatment device 925 and alternatively or additionally, a rotatable trigger 946 is attached at a lower, distal portion of the handle 942. Configured within the handle 942 is a slider 947 that is attached to the shaft or wire and is associated and cooperates with the trigger 946. A constant force spring 950 is associated and cooperates with the slider 947 to retract cutting structure of the treatment device 925 when the trigger 946 is released. Further, transillumination structure is configured within the handle 942 and includes a battery compartment 952 and an electrical switch 954 for turning on and off a light source (e.g. LED) configured at a distal end of the treatment system 940.

Pulling the trigger 946 completely results in configuring a treatment device 925 into a hooking configuration where cutting structure of the treatment device 925 is protected. Upon releasing the trigger 946 slightly, the spring 950 retracts the shaft or wire associated with the treatment device 925, and positions the shaft or wire within a detent on the slider 947 to signal the user with a tactile feedback that the cutting structure of the treatment device 925 is exposed.

Full release of the trigger 946 results in the spring 950 retracting the shaft or wire completely to thereby place the treatment device 925 in a closed or undeployed position. The treatment system 940 can then be re-positioned and manipulated again to treat additional areas.

Figure 12A:
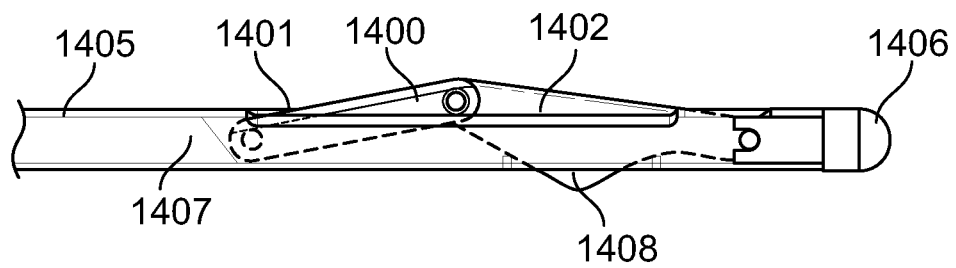
FIGS. 12A-C are top views, depicting a further approach to a treatment system.
Figure 12B:
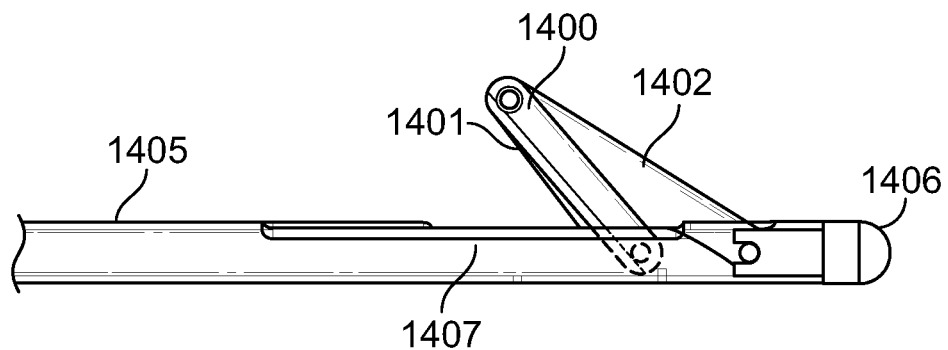
Figure 12C:
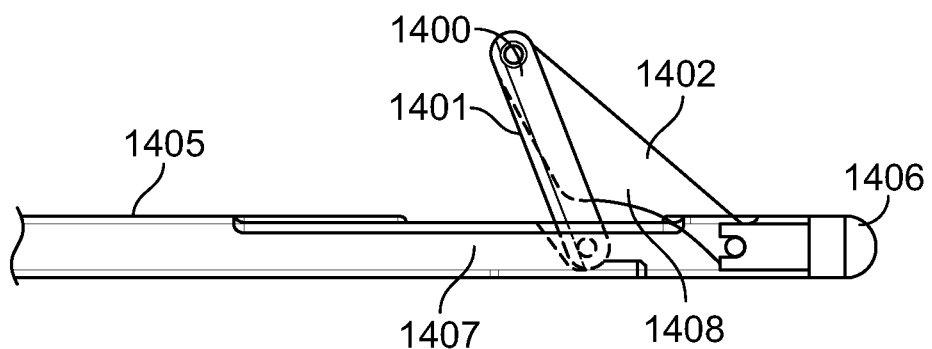

Various additional embodiments of treatment devices are described in FIGS. 12A-18C. With reference to FIGS. 12A-C, the cutting, slicing or disrupting treatment assembly is again defined by a projecting linkage arrangement. A first link 1400 includes a blade 1401 and is rotatably attached at one end to a second link 1402. The opposite end of the first link 1400 slides with respect to a longitudinal shaft 1405 (shown as at least partially transparent). The shaft 1405 defines a housing for supporting and containing the linkage arrangement. A second end of the second link 1402 is rotationally affixed to a distal point on the shaft 1405. A drive shaft or push rod 1407 is rotatably or pivotably attached to the opposite end of the first link 1400 and the second link 1402 includes a generally triangular or pointed projection 1408 that is sized and shaped to shield the blade 1401 from contacting tissue when the assembly is placed in a hooking configuration. When the push rod 1407 is fully retracted (FIG. 12A), the blade 1401 is sheathed within the body of the longitudinal shaft 1405. It is noted that in the fully retracted configuration that the first and second links 1400, 1401 form an obtuse angle and the projection 1408 extends a relatively small distance from an opposite side of the longitudinal shaft. When the push rod 1407 is advanced completely to a stop, the projection 1408 contacts the push rod 1407 and the blade 1401 is again protected by the projection 1408 (FIG. 12B). It is in this configuration that the treatment device can be used to hook target septa and to test septa to determine if such septa is associated with the expression of cellulite on a patient's skin. Withdrawing the push rod 1407 from its fully advanced position and on the order of about 0.070 inches in one embodiment (See FIG. 12C where the blade 1401 is shown transparent for illustrative purposes), the blade 1401 is exposed and presented for engaging and cutting, slicing or disrupting target septa. The treatment device also has a blunt, atraumatic tip 1406 that allows the treatment device to be advanced through the subcutaneous tissue with little trauma. In all embodiments, blunt tip 1406 can house a light emitting diode, be a light emitting diode or house the end of a light fiber in order to facilitate transillumination through the skin for the user to use for guidance in knowing the location of the tip of the treatment device.

It is to be recognized that additionally or alternatively, the tip in any of the disclosed embodiments can be shaped so as to be characterized by or associated with a low introduction and advancement force through and within the patient's skin and anatomy, while also presenting a low likelihood of damaging tissue. Accordingly, the tip can assume bullet point or short dilator tip shapes, or can define a sharp profile or a trocar-type configuration for ease of advancement or tracking. Additionally, the tip can be retractable, reconfigurable or otherwise define a sharpened structure only when the tip is presented with a pre-determined level of resistance. In one particular approach, a spring loaded cover or shield is configured about the tip such that when presented with a defined resistance, the cover or shield is removed to expose a sharpened tip configured to facilitate advancement of the treatment device or reduce the force to cross patient anatomy.

Figure 13A:
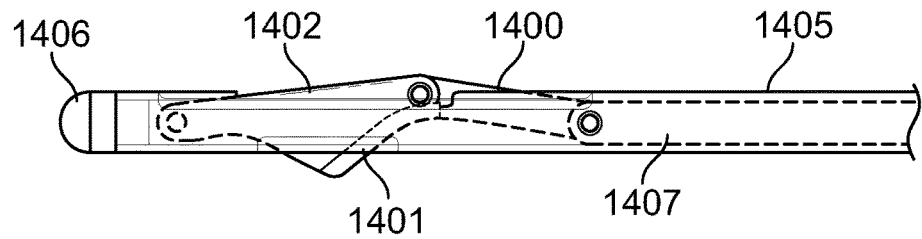
FIGS. 13A-F are bottom and top views, depicting yet another further approach to a treatment system.
Figure 13B:
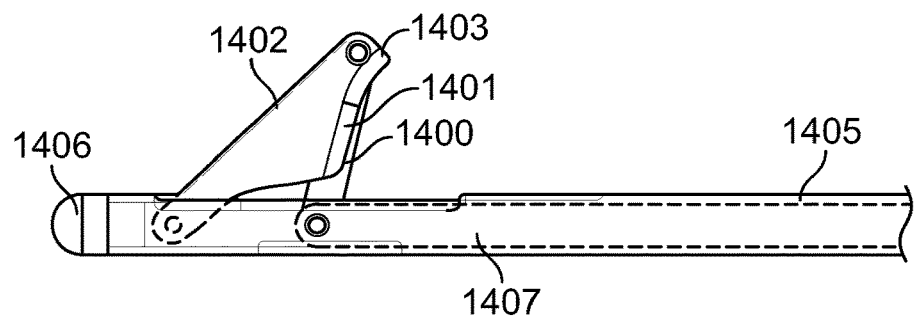
Figure 13C:
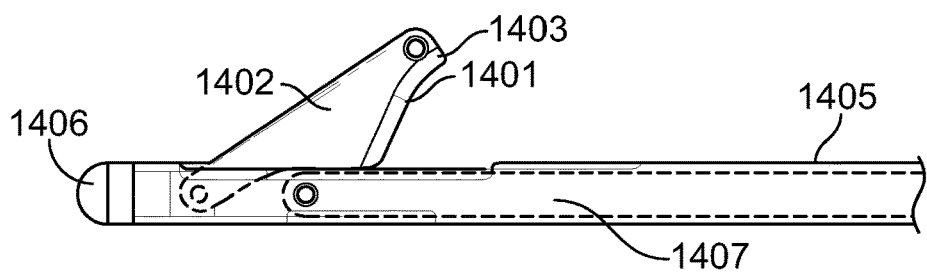
Figure 13D:
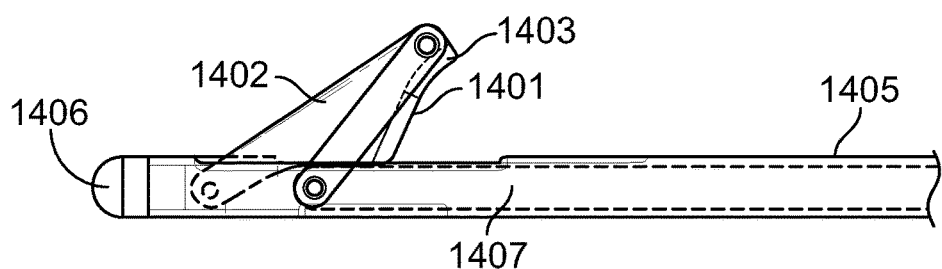

In an alternative approach (FIGS. 13A-D). the second link 1402 includes a blade 1401 that has a sharpened protrusion 1403, and the first link 1400 functions as a blocker to shield a main portion of the blade 1401 from contacting tissue when the treatment device is in the hooking configuration. When the treatment device is in the hooked configuration, the sharpened protrusion 1403 extends proximally from the pivot between the first link 1400 and second link 1402 so that as the treatment device is pulled proximally by the user, the pivot location, as the leading portion of the device during retraction, does not get snagged in tissue but rather slices through it so the user can hook and feel resistance of septa with the main portion of the first link 1400. Notably, in a fully retracted position (FIG. 13A), the first and second links 1400, 1401 define an obtuse angle and when the push rod 1407 is advanced nearly completely (FIG. 13B), a majority of the blade 1401 is protected by the second link 1402. As such, structure is presented in a hook-form both to encourage hook capture as well as provide a portion of unprotected blade 1403 near the connection between the first and second 1400, 1402 links. Completely advancing the push rod 1407 fully exposes the blade 1401 for cutting, slicing or disrupting target septa (See FIGS. 13C-D; FIG. 13D showing the first blade as transparent for illustrative purposes) as the treatment device is retracted proximally by the user.

Figure 13E:
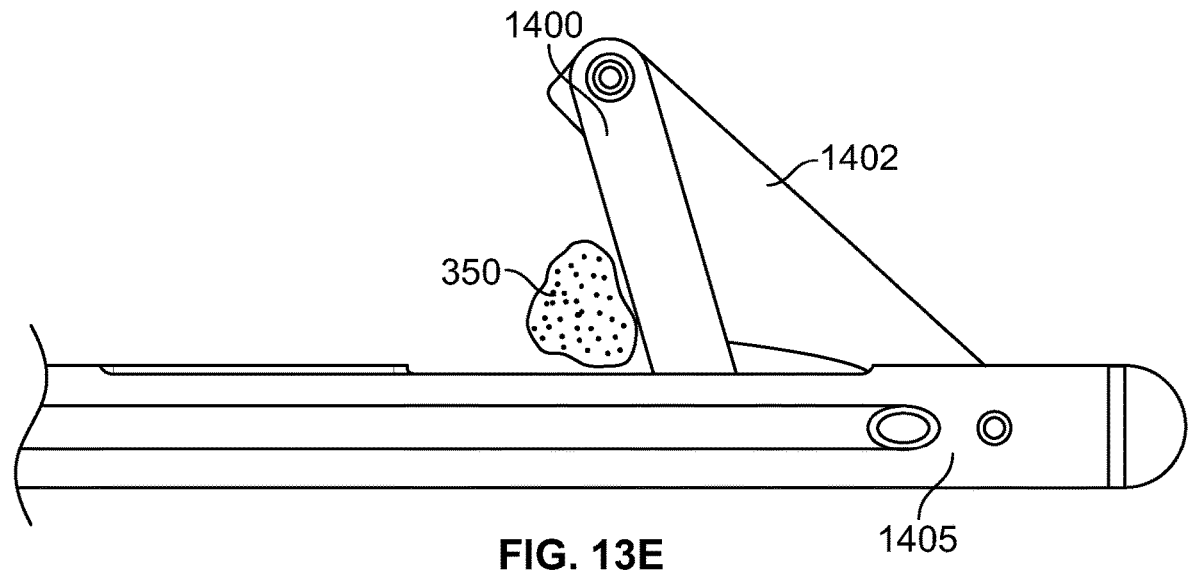
Figure 13F:
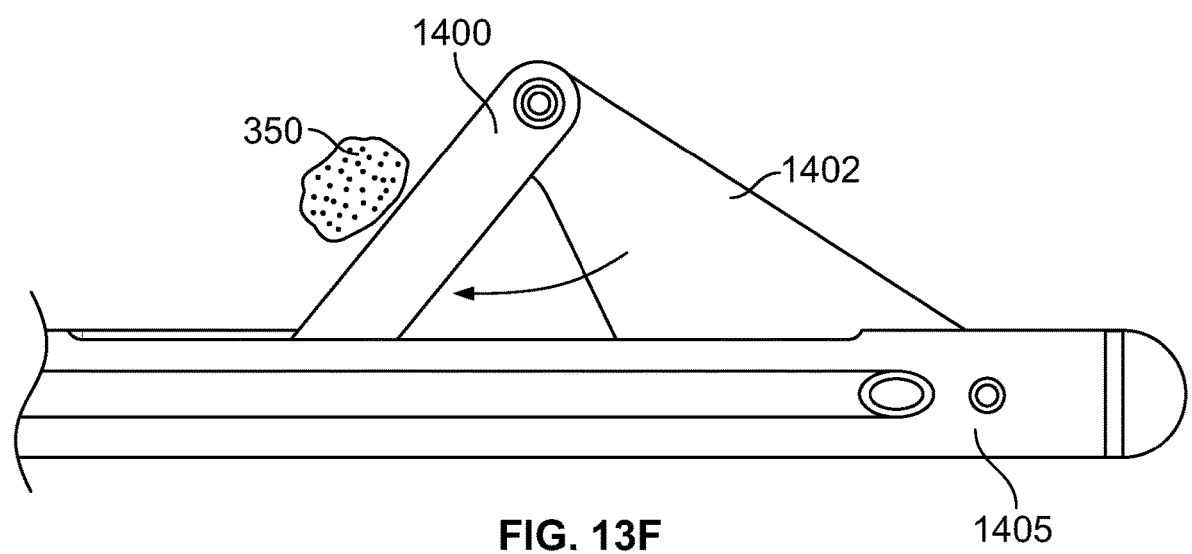
Figure 14A:
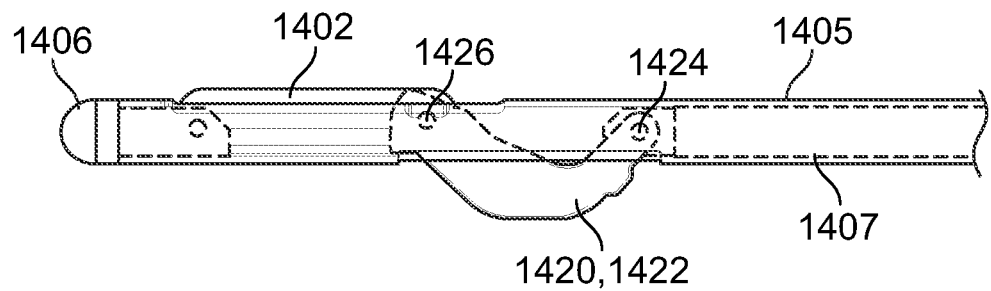
FIGS. 14A-F are bottom and perspective views, depicting another embodiment of a treatment system.
Figure 14B:
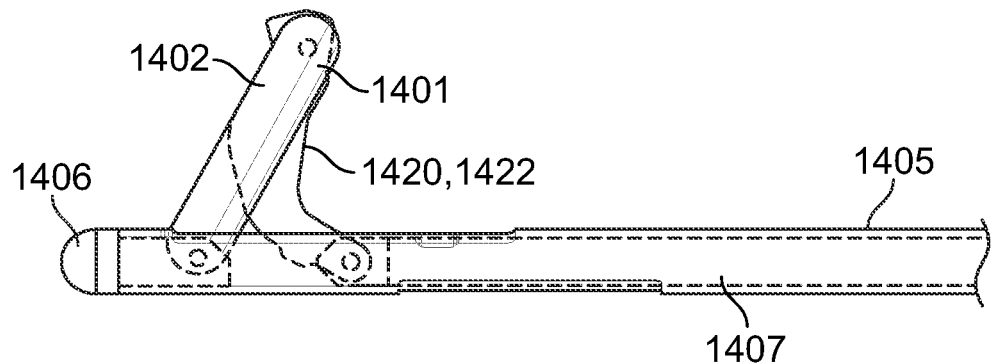
Figure 14C:
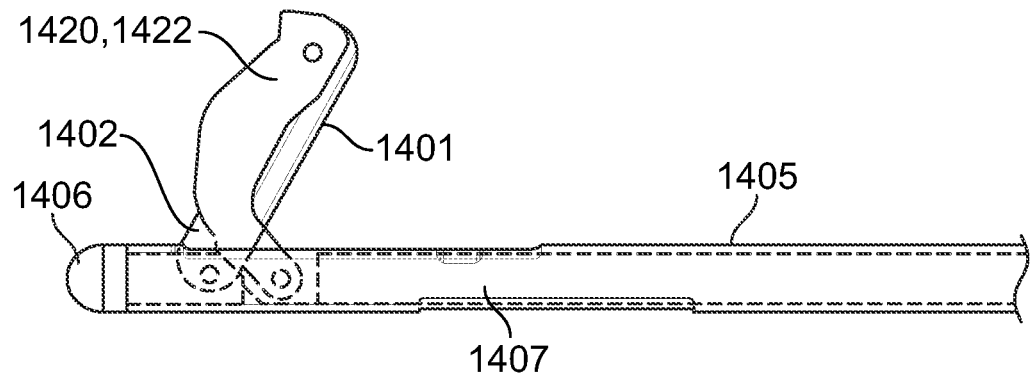
Figure 14D:
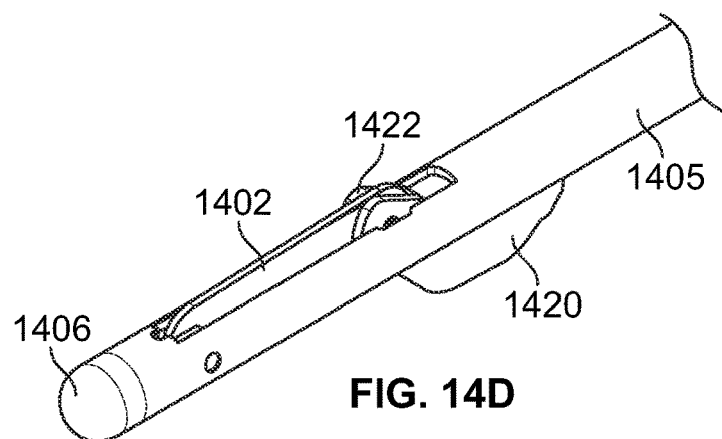
Figure 14E:
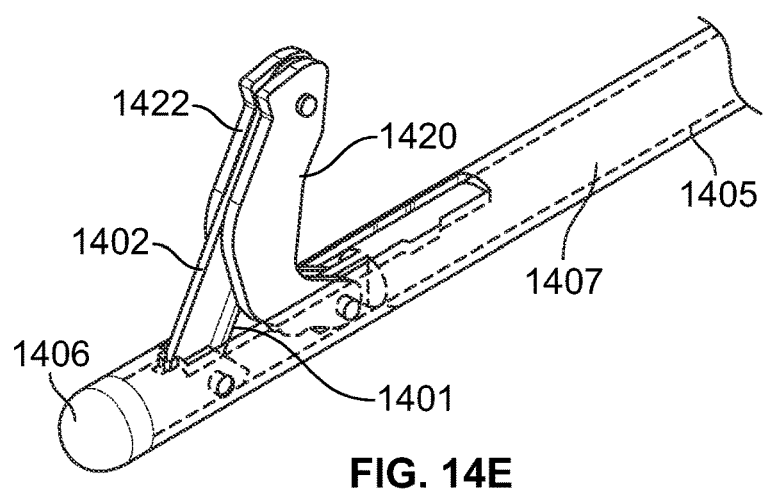
Figure 14F:
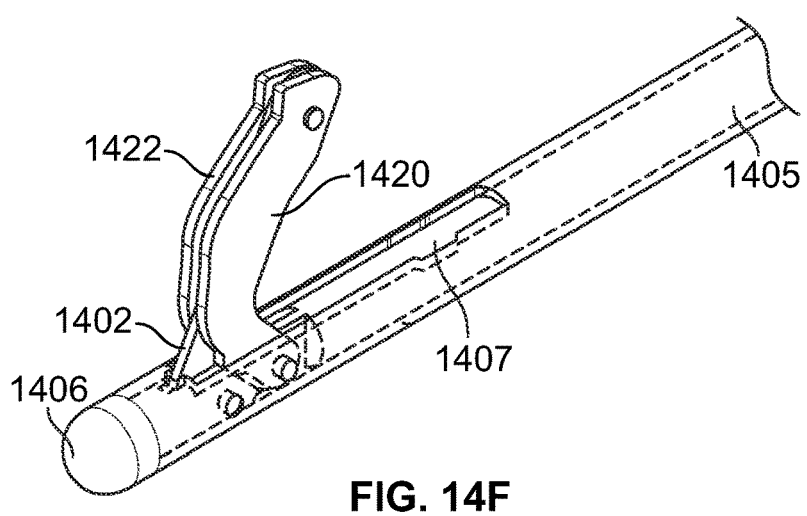
Figure 15A:
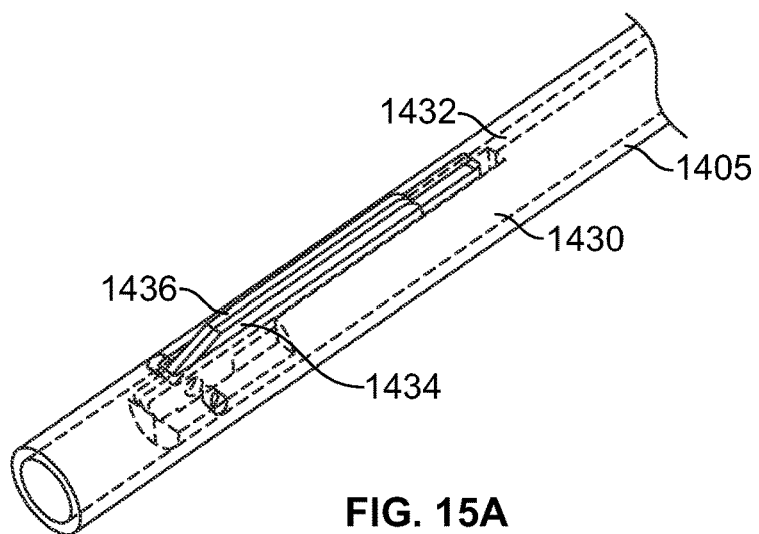
FIGS. 15A-F are perspective and top views, depicting yet another embodiment of a treatment system.
Figure 15B:
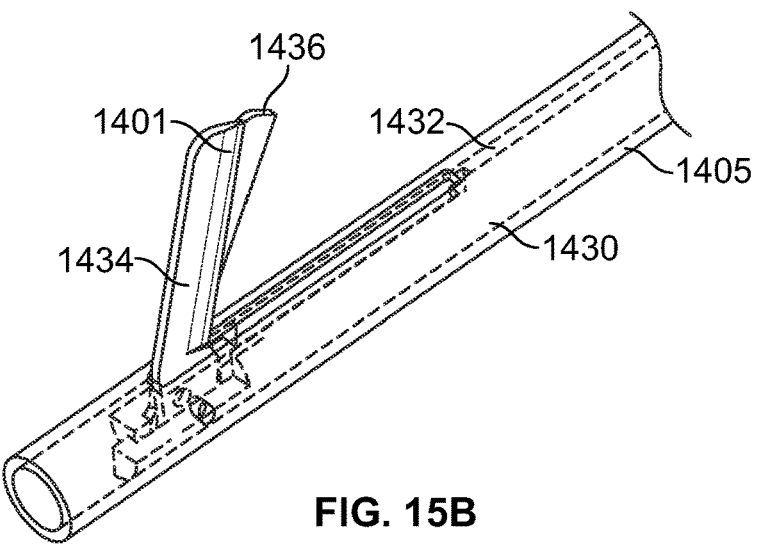
Figure 15C:
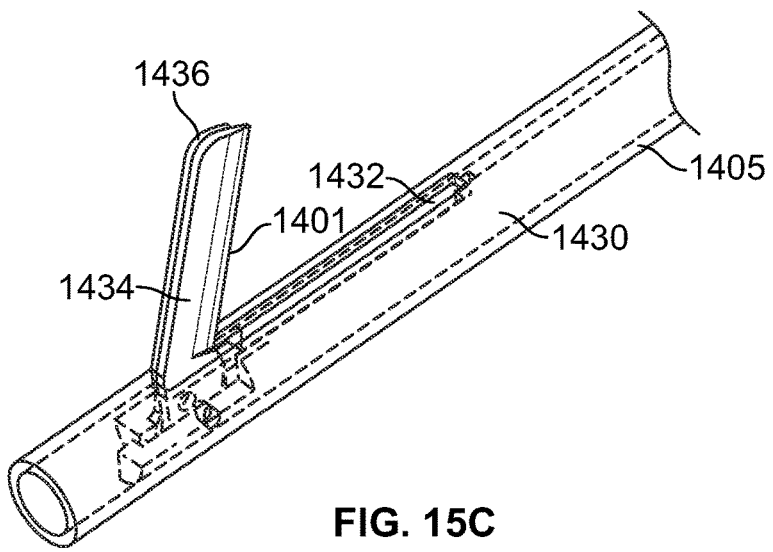
Figure 15D:
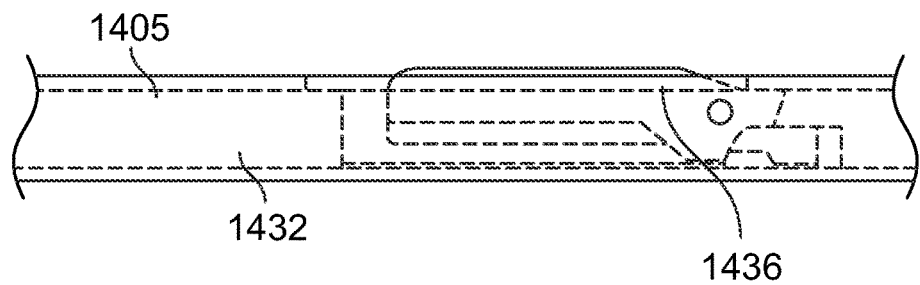
Figure 15E:
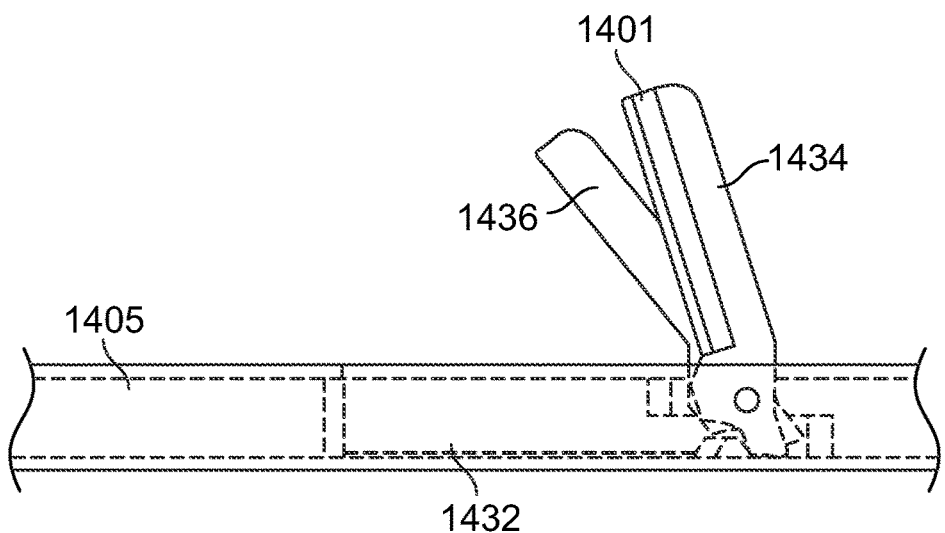
Figure 15F:
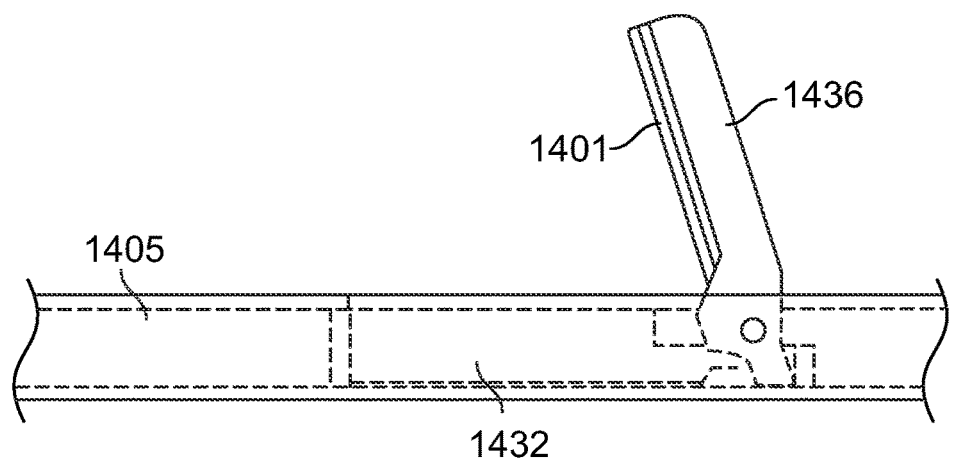

In employing one or more of the disclosed embodiments in a treatment procedure, there is an expectation that there are instances where it is preferable to not disrupt a hooked septa, and in such a case it is desireable to release or disengage the hooked septa. In certain approaches, to release or disengage, the treatment device would be advanced or twisted away from the hooked septa. It is thus recognized that a challenge exists in that there may be additional septa or other tissue in the area which could be unintentionally re-engaged by the treatment device when it is in a hooking configuration, and stowing of the treatment device may be inhibited by adjacent patient anatomy. With reference to FIGS. 13E-F, treatment devices that include a hinge link arrangement 1400, 1402 or similar structure that transition from a hooked configuration (FIG. 13E) toward a stowed configuration (FIG. 13F) by pivoting relative to the longitudinal shaft 1405, benefit from the blocking link 1400 (or similar structure) moving to push septa 350 or other tissue away from the treatment device as the treatment device is being sheathed or stowed. This action requires no additional advancement of the treatment device within patient anatomy and ensures that septa 350 or other tissue do not become undesirably entrapped. Moreover, when being stowed the links 1400, 1402 dislodge any tissue that might have become captured within the longitudinal shaft 1405 and the links 1400, 1402 ultimately occupy such spaces within the longitudinal shaft 1405.

Turning now to FIGS. 14A-F, there is shown yet another approach to a treatment device. Here, there are provided two parallel arranged and articulating first links 1420, 1422 arranged to block or shield a blade 1401 attached to or forming an edge of a second link 1402. The first links 1420, 1422 each define a curved or yoke-shaped member with a unique profile designed to selectively shield the second link 1402, a first end 1424 of each rotatably or pivotably attached to a pusher 1407 and second ends 1426 rotatably or pivotably attached to the second link 1402. The parallel arranged first links 1420, 1422 provide additional strength for the hooking and cutting positions. When the push rod 1407 is fully retracted (FIGS. 14A and 14D), a curved portion of the first links 1420, 1422 projects from an opposite side of the longitudinal shaft 1405 (shown at least partially transparent) from which the links extend when deployed for hooking or cutting, slicing or disrupting septa. To present tissue hooking structure, the push rod 1407 is advanced so that the first links 1420, 1422 completely shield or block the blade 1401 (See FIGS. 14B and 14E; one first link 1420 is shown as transparent for illustrative purposes in FIG. 14E) from contacting tissue. Advancing the push rod 1405 completely operates to fully expose the blade 1401 (See FIGS. 14C and 14F) and thus present the blade 1401 for cutting, slicing or disrupting target tissue.

As shown in FIGS. 15A-F, a treatment device can alternatively or additionally include first and second push rods 1430, 1432, the first push rod 1430 configured to manipulate an articulating or pivoting first link 1434 and the second push rod 1432 configured to manipulate an articulating or pivoting second link 1436 that includes a blade 1401 surface. When the push rods 1430, 1432 are in a fully advanced position (FIGS. 15A and 15D), the first 1434 and second 1436 links are generally parallel and stowed within the longitudinal shaft 1405 (shown at least partially transparent). Withdrawing the push rods 1430, 1432 operate to project the first 1434 and second 1436 links from the stowed position (See FIGS. 15B, C, E, F). Withdrawing the push rods equally results in the first link 1436 overlaying yet fully exposing the blade 1401 (FIGS. 15C and 15F) for cutting, slicing or disrupting target tissue, but when the push rod 1430 associated with the first link 1434 is advanced to a different degree than the second push rod 1432, a portion of the blade 1401 can be shielded or blocked by the first link 1434 (FIG. 15B) thereby presenting structure for hooking target tissue, or a portion of the blade 1401 can be shielded (FIG. 15E) thus presenting both hooking and cutting structures. This embodiment could also have blunt tip 1406.

Figure 16A:
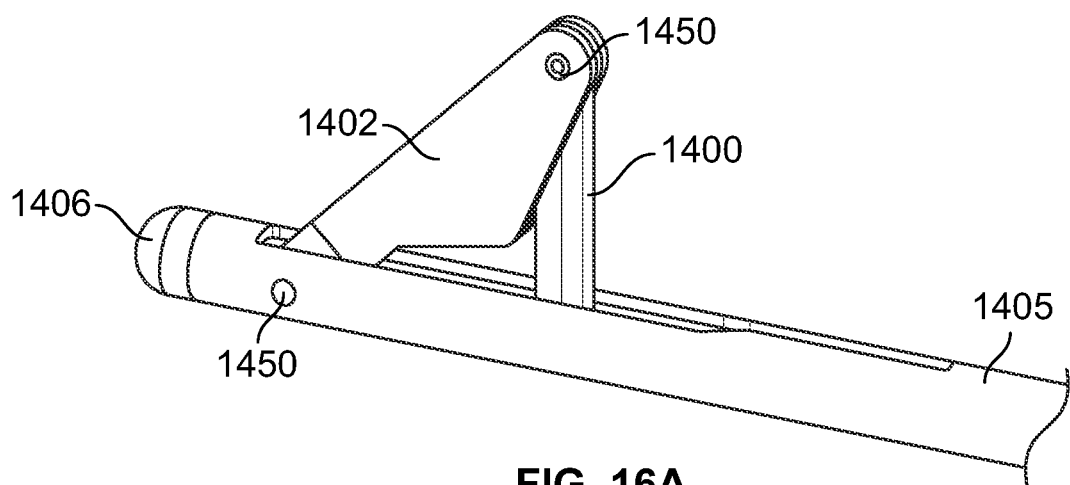
FIGS. 16A-C are perspective views, depicting alternative or additional features of a treatment system.
Figure 16B:
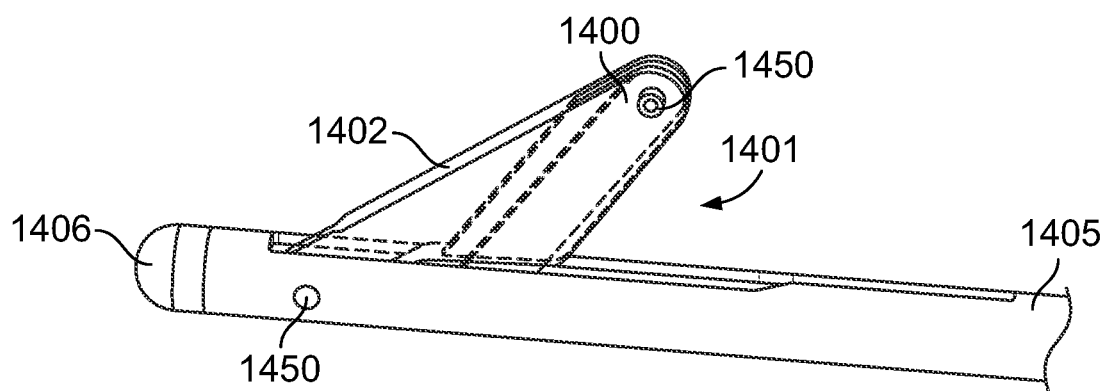
Figure 16C:
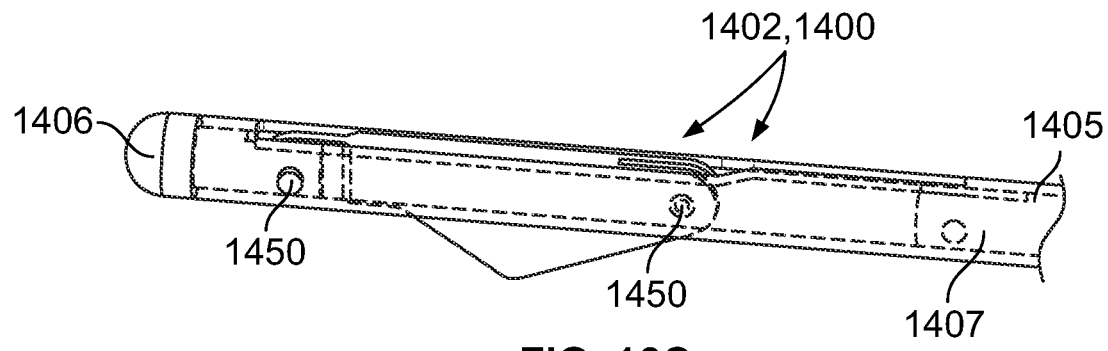

In additional or alternative aspects, the robustness of the blade mechanism of a treatment device can be enhanced by strengthening pivot points, increasing strength of the longitudinal shaft and improving blade concealment during insertion and advancement within and hooking of tissue. As shown in FIG. 16A, a welded pin or swaged tube 1450 can be used at the connection between first 1400 and second link or links 1402. Also, mechanical joining such as a welded pin or swaged tube can form the connection between second link or links 1402 and a distal portion of the longitudinal shaft 1405. Such pivot points can in one or more embodiments be defined by about 0.025 inch diameter pins or tubes, for example, and can be used at one or more rotating or pivoting connections of a treatment system. Moreover, as best seen in FIGS. 16B-C, a first link 1400 including a blade 1401 can be configured between a pair of second links 1402 (one link shown as transparent) rather than concealed by or cooperating with a single first link 1400.

Figure 17A:
FIGS. 17A-C are perspective views, depicting further features of a treatment system.
Figure 17B:
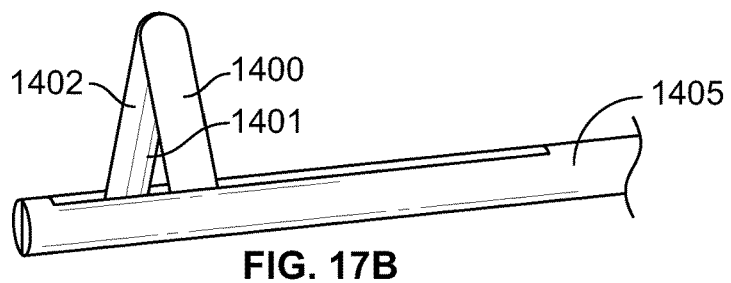
Figure 17C:
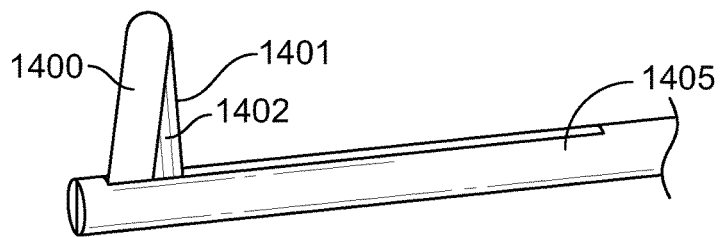

As shown in FIGS. 17A-C, in an alternative or additional approach, a treatment system lacks projecting structure when the links 1400, 1402 are fully retracted and housed within the longitudinal shaft 1405 (FIG. 17A). The first link 1400 acting as a blocking or blunt element can be spring loaded so that it shields the blade 1401 formed on the second link 1402 (FIG. 17B) until a critical force is achieved and then the blade 1401 is presented (FIG. 17C) for cutting, slicing or disrupting target septa. After cutting or slicing, the blade 1401 can be configured to automatically be re-sheathed or an actuator such as a button can be provided to re-sheath the blade 1401. In such approaches, there is two positions of the links, namely sheathed and deployed. The same reduces the overall force requirements since there is not a condition where a user employs the hooking structure at too high of a force. Thus, the blade 1401 is fully sheathed or contained within the longitudinal shaft 1405 during navigation, and deployed when necessary. In this way, the longitudinal shaft 1405 can be formed from a hypotube for example, with fewer cuts for ejecting and storing the links 1400, 1402. Such structure or related functionality can be incorporated into any of the disclosed embodiments to thus provide spring-loaded cutting to require a certain, controlled amount of force to expose the blade for cutting. This embodiment could also have blunt tip 1406.

Figure 18A:
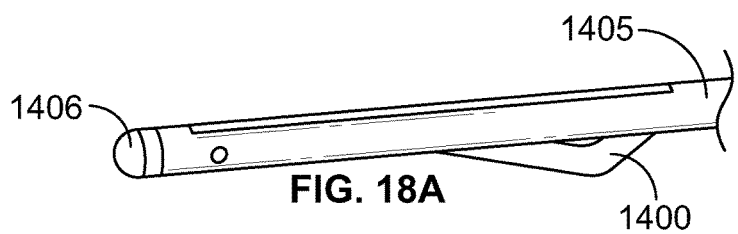
FIGS. 18A-C are perspective views, depicting yet further features of a treatment system.
Figure 18B:
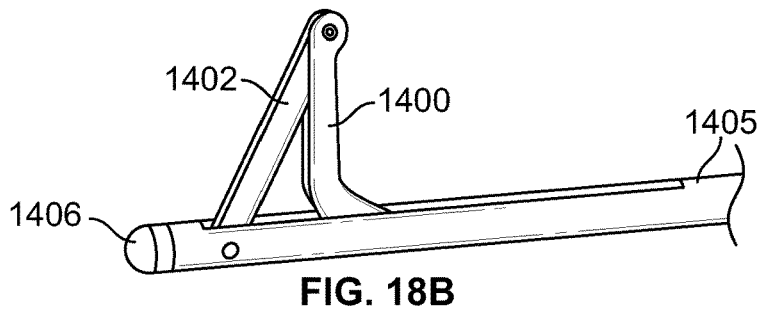
Figure 18C:
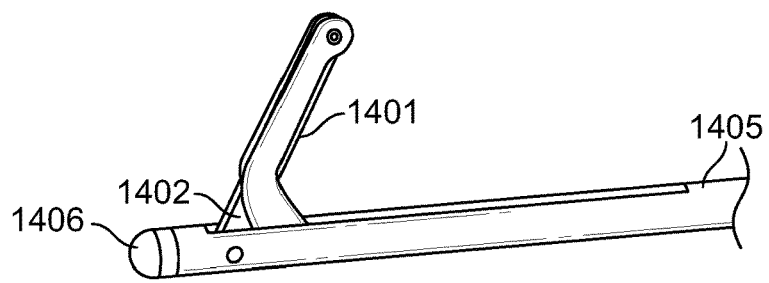

In a related approach (See FIG. 18A-C), the blocking or hooking function is provided by a pair of curved or angled first links 1400. In a stowed configuration, the curved or angled links 1400 project from an opposite side of the longitudinal shaft 1405 from the deployed or treatment side of the shaft 1405 (FIG. 18A). However, like the immediately preceding approach, the blocking or shielding first links 1400 are spring loaded so that they reside on opposite sides and shield the blade 1401 (FIG. 18B) until a critical force is achieved and then the blade is exposed (FIG. 18C) for cutting, slicing or disrupting target septa. Again here, after cutting or slicing, the blade 1401 can be configured to automatically be re-sheathed or an actuator such as a button can be provided to re-sheath the blade 1401, and there is two positions of the links, namely sheathed and deployed.

Figure 19A:
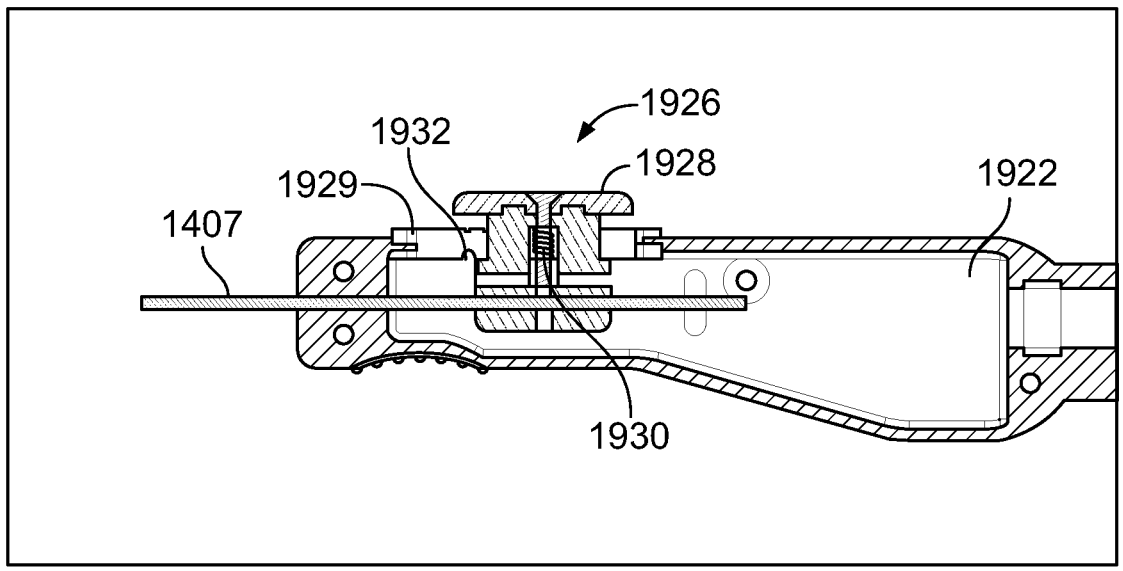
FIGS. 19A-B are side views partially in cross-section, depicting alternative or additional features of a handle for a treatment system.
Figure 19B:
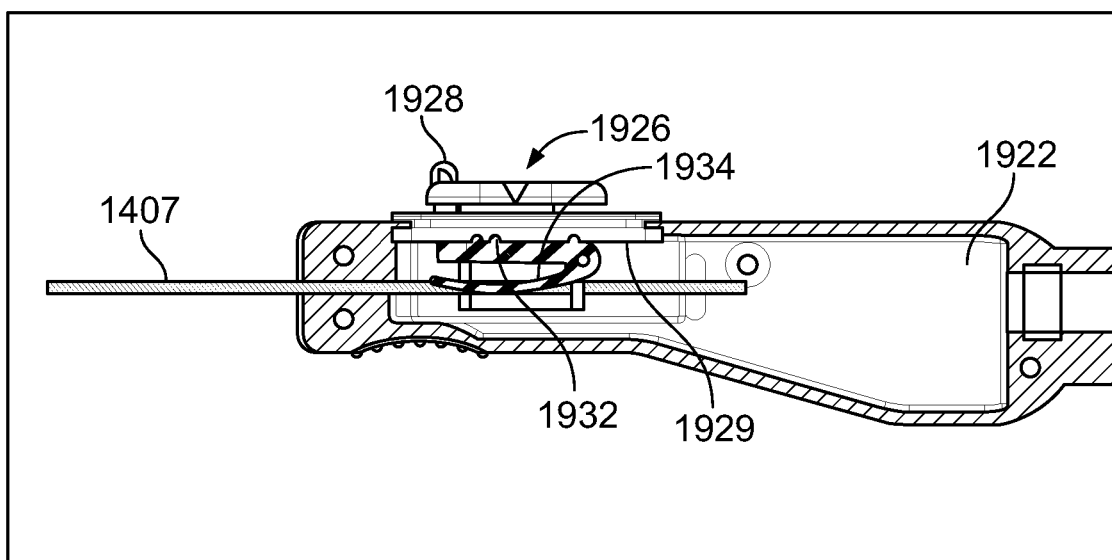

With reference now to FIGS. 19A-B, there is shown a handle 1922 of a treatment device that includes a trigger or slider assembly 1926 that includes a depressible button 1928. The handle 1922 includes a track 1929 along which the button 1928 is registered. Such an arrangement can be incorporated into one or more of the previously disclosed treatment systems. As shown in FIG. 19A, the button 1928, in one embodiment, is biased relative to the track 1929 by a helical spring 1930. The slider assembly 1926 is attached to a drive shaft or pusher 1407 that is connected to and facilitates manipulation of a treatment device (not shown). The button 1928 is depressible to release a locking or other engagement between the button 1928 and the track 1929 so that the slider assembly 1926 can be slid relative to the handle 1922. Releasing the button 1928 results in allowing the button to engage the track 1929 and slide into locking engagement with one of a series of cut-outs 1932 formed in the track 1929. It is to be noted that when not locked to the track 1929, the button 1928 of slider assembly can engage and slide along the track 1929 between locking positions. Such cut-outs 1932 are arranged and located so that when the slider assembly 1926 is locked to the track 1929, the treatment device is positioned in one or more of sheathed, hooking or cutting positions within tissue and relative to target septa. A secure engagement between the slider assembly 1926 and the handle 1922 is thus provided as is tactile feel to the user concerning the positioning and state or configuration of the treatment device. As shown in FIG. 19B, rather than a helical spring, the button 1930 is biased by a leaf spring 1934. Also, here, the button 1928 is configured to be separately actuatable and defines an independently depressible structure from the sliding structure of the slider assembly 1926 to thereby provide alternative discrete control of sliding and locking functions.

Figure 20A:
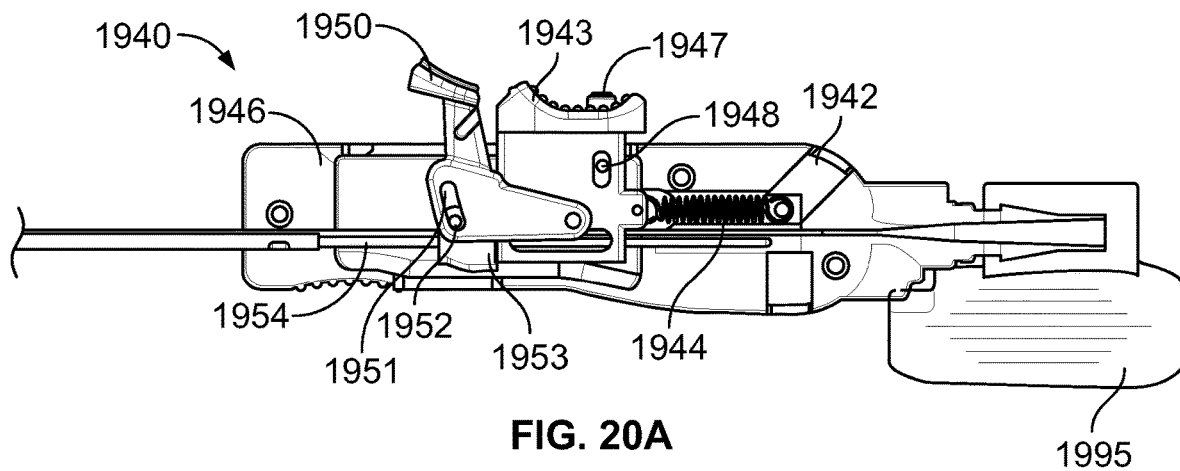
FIGS. 20A-F are side partial cross-sectional and top views, depicting a further embodiment of a treatment system.
Figure 20B:
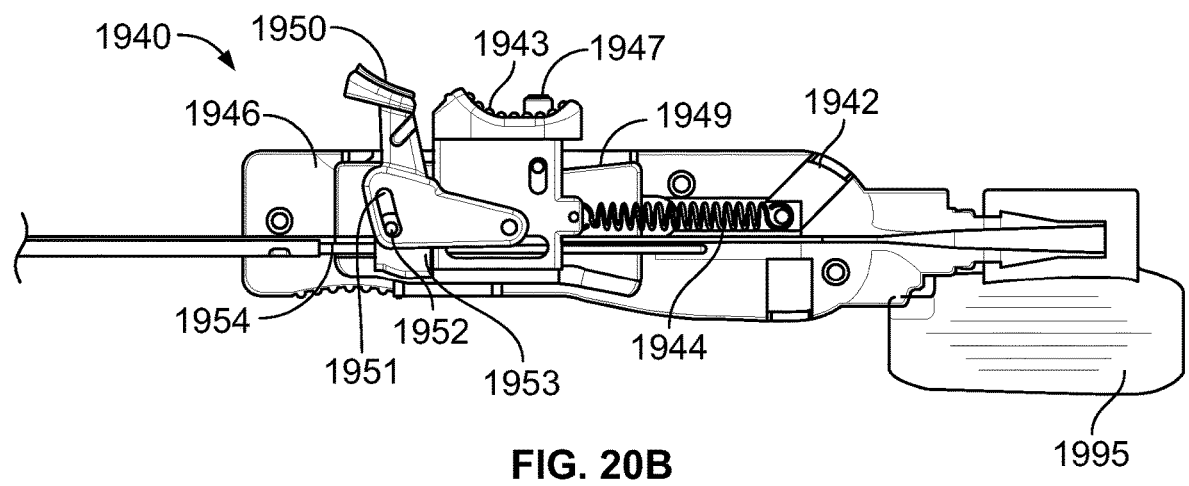
Figure 20C:
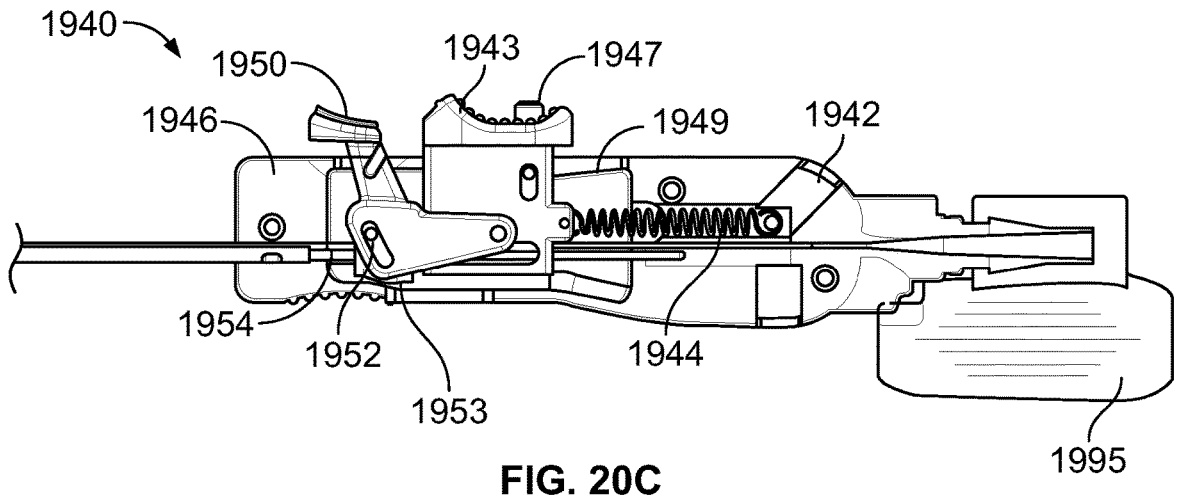
Figure 20D:
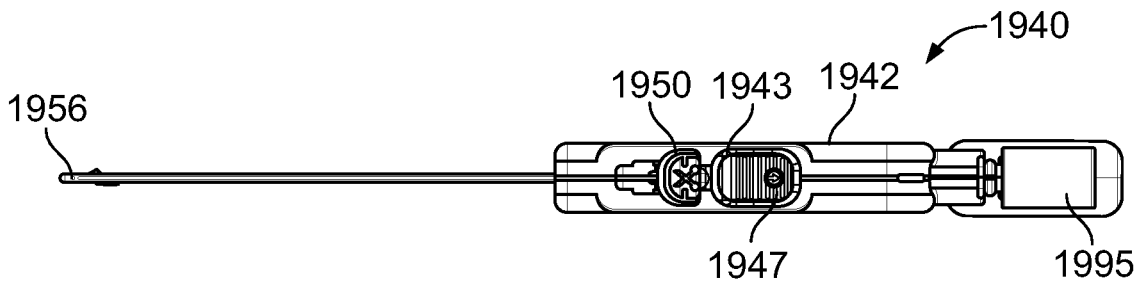
Figure 20E:
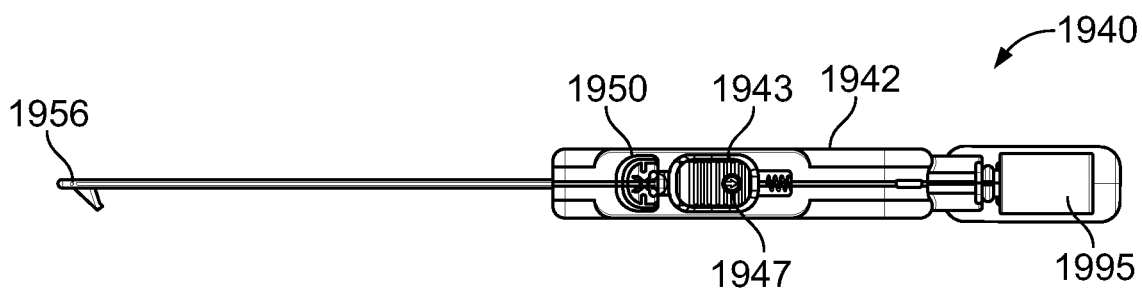
Figure 20F:
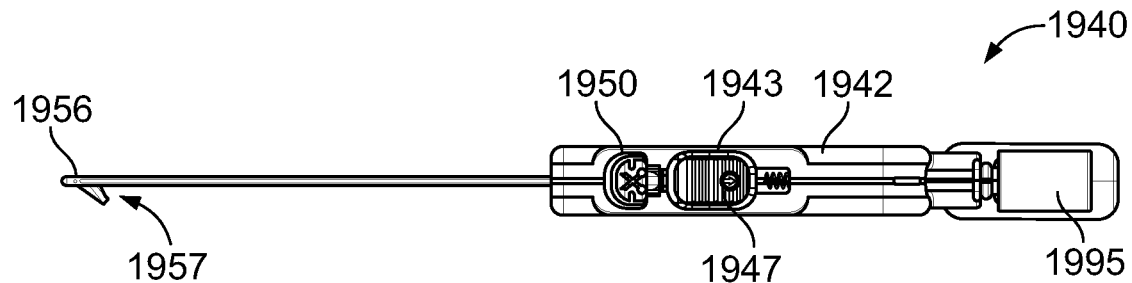
Figure 21A:
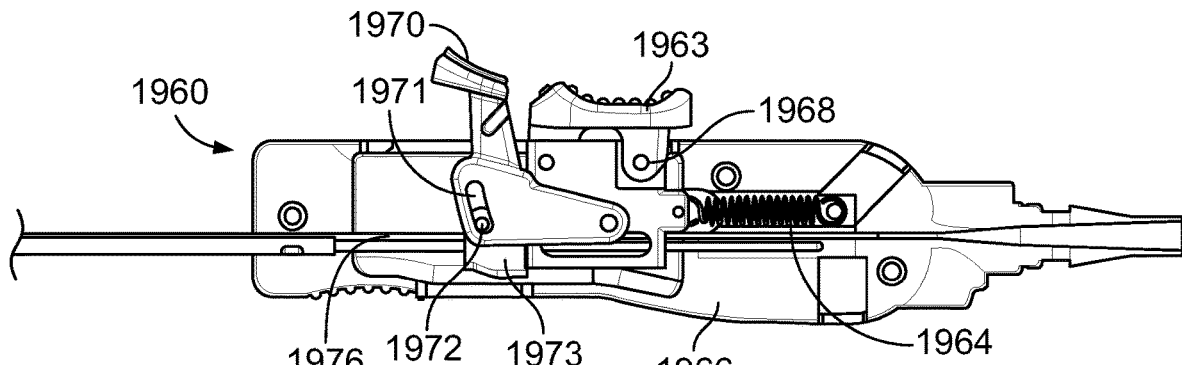
FIGS. 21A-C are side partial cross-sectional views, depicting another approach to a handle assembly for a treatment system.
Figure 21B:
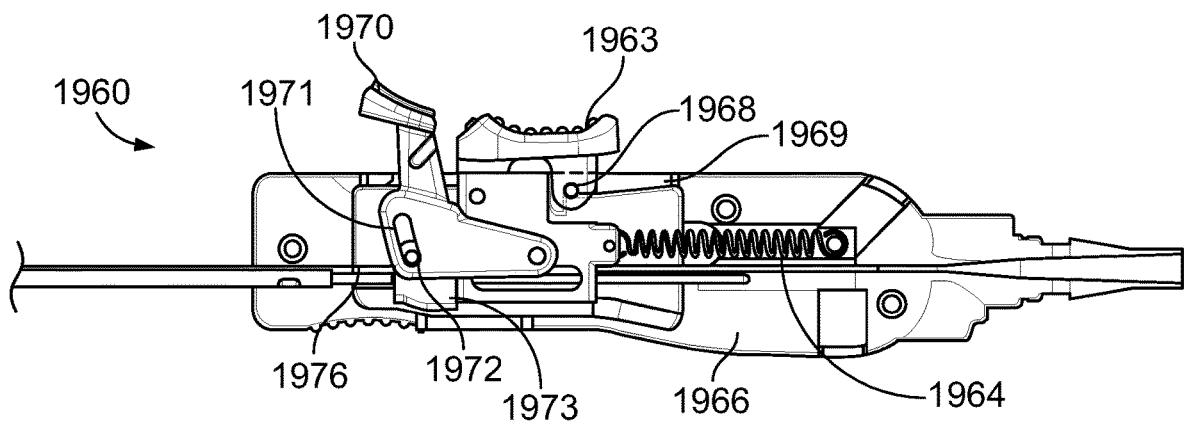
Figure 21C:
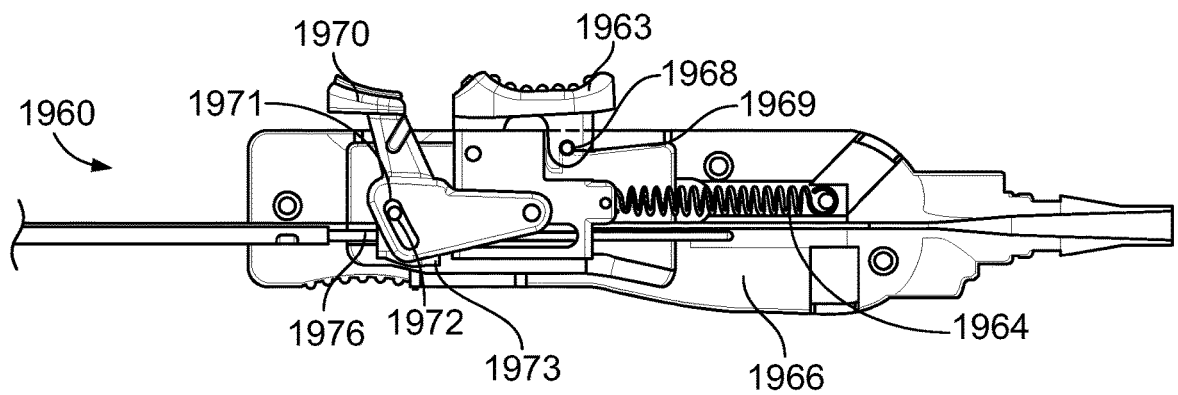

Further approaches to treatment systems are depicted in FIGS. 20A-22C. As shown in FIGS. 20A-C, a treatment system 1940 includes a handle assembly 1942 that includes a slider 1943 biased by a spring 1944, the slider 1943 is configured to be translated along a portion of a body 1946 of the handle assembly 1942. A button 1947 projects vertically from an upper surface of the slider 1943, the button 1947 being connected to or associated with a boss 1948 that rides within a slot formed in the slider 1942. The boss 1948 also slides along and is configured to be registered along a ramp 1949 or other engaging structure formed within the handle body 1946. Also, rotatably attached to the slider 1943 is a lever 1950 that includes a curved slot 1951 that receives a boss 1952 projecting from a bracket 1953. Each of the slider 1943 and the bracket 1953 are attached to one or more longitudinally extending members 1954 that is/are associated with a treatment device 1956 attached at a terminal end portion thereof (See FIGS. 20D-F). Attached to the proximal end of the handle assembly 1942 is an optional light and energy source unit 1995, for example, a light emitting diode and battery. Extending distally through the handle assembly 1942 and longitudinal shaft of the treatment device 1956 to the distal portion of the longitudinal shaft is a light fiber (not shown) to transmit light from the light and energy source unit 1995 to the distal portion of the treatment device 1956 to provide transillumination through the skin for the user.

In a treatment device stowed position (See FIGS. 20A and D), the slider 1943 is in its most proximal position and the spring 1944 is mostly compressed. As the slider 1943 is translated forward (FIGS. 20B and E), the spring 1944 is extended and the slider boss 1948 becomes temporarily and fixedly registered along the ramp 1949. Due to this action, the longitudinally extending member 1954 is advanced to manipulate the treatment device 1956. It is in this configuration that the treatment device 1956 is in a deployed but covered configuration intended for hooking or otherwise engaging target septa. By subsequently depressing the rotatable lever 1950, through the interaction of the lever 1950 and the bracket 1953, the longitudinally extending member 1956 is advanced slightly further in a distal direction to uncover a treatment device sharpened link or blade 1957 (See FIGS. 20C and F), the sharpened link or blade 1957 being configured for cutting, slicing or disrupting septa. Notably, a spring (not shown) is configured between the lever 1950 and bracket 1953 to bias the lever 1950 to return the treatment device 1956 to a locked and hook configuration. After desired manipulation of the treatment device 1956 at an interventional site, the slider button 1947 is depressed to release the engagement between the slider boss 1948 and the ramp 1949 to thereby permit the spring 1944 to return the slider 1943 to its most proximal position and to stow away the treatment device 1956 for further use or removal from the interventional site. In alternative approach, the system 1940 would lack the lever 1950 and an additional spring (not shown) is configured to only allow advancement of the bracket 1953 when the treatment device 1956 is presented with a pre-determined resistance, at which time the blade 1957 is permitted to be exposed. In this way, the tool is more easy to use and the cutting step subsequent to hooking septa is less likely to be omitted.

In another approach (FIGS. 21A-C), the treatment system 1960 includes a handle assembly 1962 that includes a slider 1963 biased by a spring 1964, the slider 1963 also being configured to be translated along a portion of a body 1966 of the handle assembly 1962. Here, rather than providing a button to unlock the slider 1963, the slider 1963 is configured to rotate with respect to the body 1966 and the slider 1963 itself includes a boss 1968 that slides along and is configured to be registered along a ramp 1969 or other engaging structure formed within the handle body 1966. Also, here, rotatably attached to the slider 1962 is a lever 1970 that includes a curved slot 1971 that receives a boss 1972 projecting from a bracket 1973. Each of the slider 1962 and the bracket 1973 are attached to one or more longitudinally extending members 1976 that is/are associated with a treatment device attached at a terminal end portion thereof (Not shown, but for example like the structures depicted in FIGS. 20D-F).

When a treatment device is in a stowed position (See FIGS. 21A), the slider 1962 is in its most proximal position and the spring 1964 is mostly compressed. As the slider 1962 is translated forward (FIG. 21B), the spring 1964 is extended and the slider boss 1968 becomes temporarily and fixedly registered along the ramp 1969, and the longitudinally extending member 1976 is advanced to manipulate the treatment device. It is in this configuration that the treatment device is in a deployed but covered configuration intended for hooking or otherwise engaging target septa. Thereafter, by depressing the rotatable lever 1970, through the interaction of the lever 1970 and the bracket 1973, the longitudinally extending member 1976 is advanced slightly further in a distal direction to uncover a treatment device sharpened link or blade (See FIG. 21C). In this configuration, the treatment device is configured to cut, slice or disrupt target septa. A spring (not shown) is configured between the lever 1970 and bracket 1973 to bias the lever 1970 to return the treatment device to a locked and hook configuration. After desired manipulation of the treatment device at an interventional site, the slider 1962 is depressed and rotated to release the engagement between the slider boss 1968 and the ramp 1969 to thereby permit the spring 1964 to return the slider 1962 to its most proximal position and to stow away the treatment device.

Figure 22A:
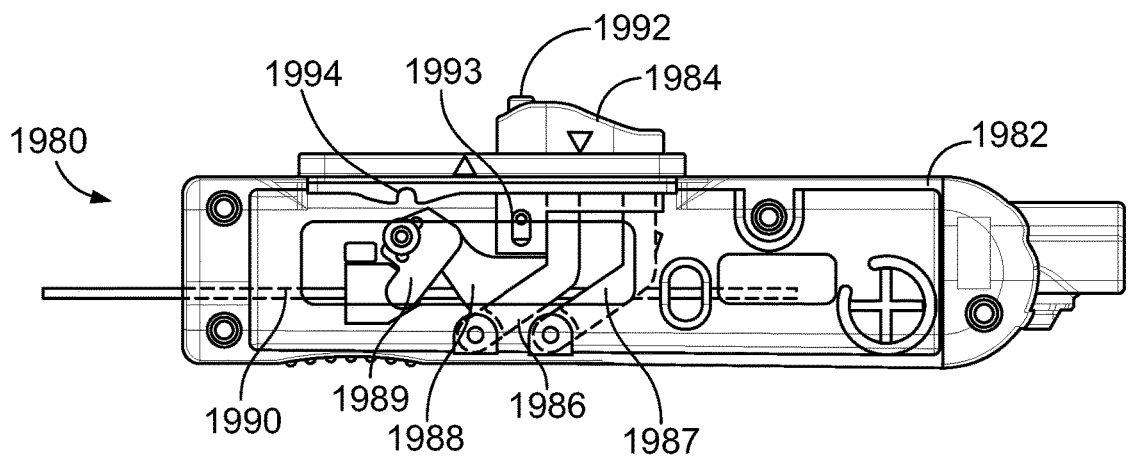
FIGS. 22A-C are side partial cross-sectional views, depicting yet another approach to a handle assembly for a treatment system
Figure 22B:
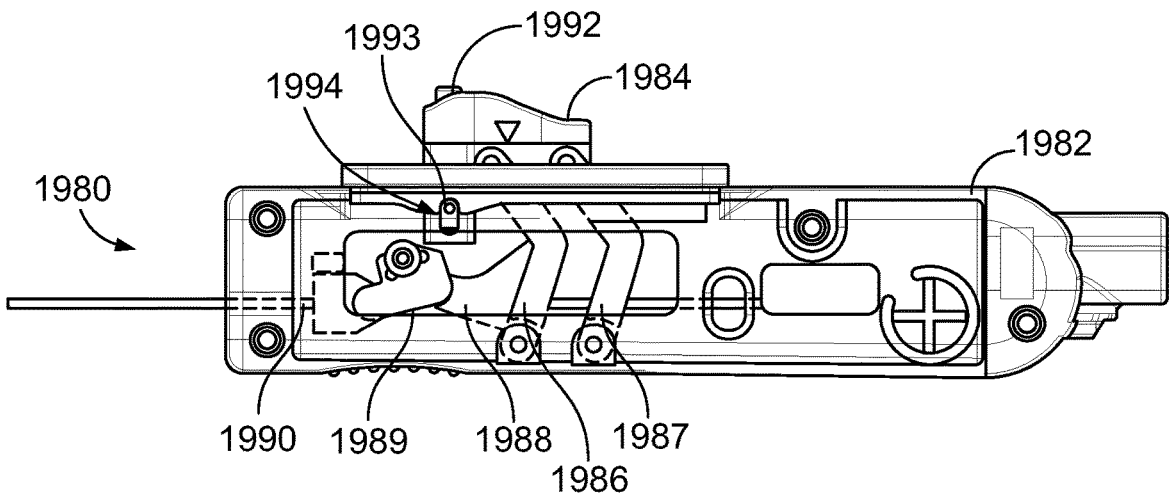
Figure 22C:
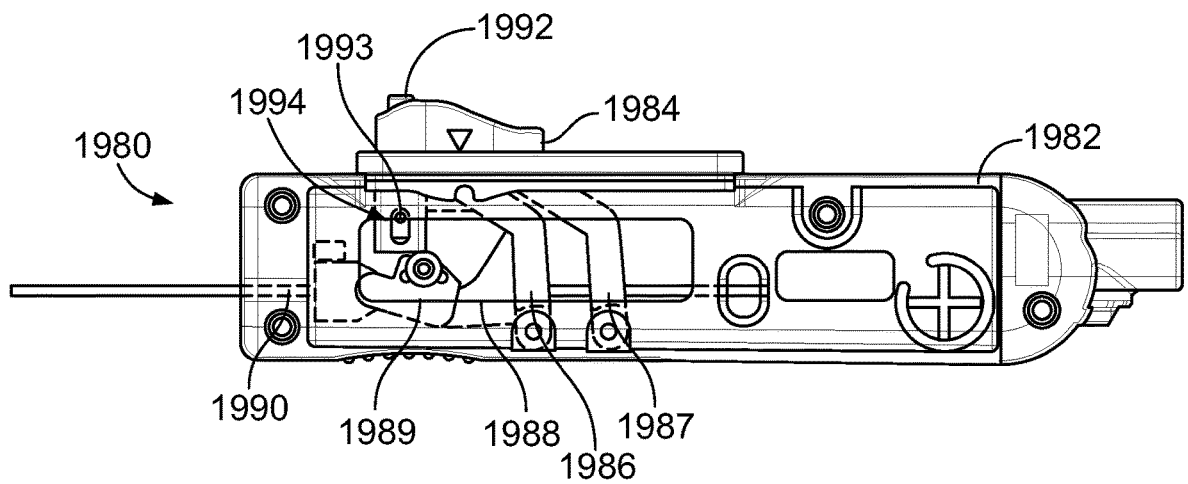

As shown in FIGS. 22A-C, the treatment device 1980 can additionally or alternatively include a handle assembly 1982 that includes a slider 1984 configured to slide along a body of the handle assembly 1982. When the slider 1984 is in its most proximal position (FIG. 22A), the treatment device (not shown) is in a stowed position. The slider 1984 is attached to a pair of rotatable, angled members 1986, 1987, the ends of each of which are rotatably attached to the the handle body and to the slider 1984, respectively. The forwardly positioned rotatable member 1986 further includes an extension 1988 that is rotatably attached to a rotatable bracket 1989 that is in turn rotatably attached to a longitudinally extending member 1990 that has a treatment device (not shown) attached to a distal end portion thereof. A button 1992 projects vertically from the slider 1984 and the button 1992 is associated with a boss 1993 that is configured to be registered along a portion of the body of the handle assembly 1982 (See FIG. 22B). When so positioned with the slider 1984 advanced along the handle body and the boss 1993 registered within a recess 1994 formed in the handle body, the treatment device is deployed but covered at least partially to present structure for hooking or engaging target septa. By depressing the button 1992, the boss 1993 of the slider 1984 can be disengaged from the recess 1994 to thereby permit the slider 1992 to be advanced further distally. In doing so, the longitudinally extending member 1990 can be advanced further to expose a cutting portion of a treatment device for cutting, slicing or engaging tissue and accomplishing desired interventional treatments. The slider 1992 can then be returned to either of the stowed or deployed but covered positions as desired for further interventional steps. Accordingly, this approach provides a mechanism that scales up small movements of the handle assembly so that the configuration of the treatment device (e.g., contained, hook or cut positions) is made more obvious to the user.

In the previous embodiments described, a "ball point pen" type of mechanism can be used in the handle assembly such that after the hook and/or sharpened edge have torn or cut through septa, the linkage automatically restows upon a sudden reduction in force on the linkage as it tears or cuts through the septa.

In another embodiment, a coil is deployed from the distal portion of the treatment device and rotated to wind the septa into the coil to re-create the targeted cellulite on the skin surface, then the coil is pulled by the user to disrupt or cut the septa or a cutter is used to sever the septa.

Accordingly, various approaches to cellulite treatment methods and apparatus are presented. The disclosed approaches are configured to provide an effective and focused approach to treating, minimizing and preventing cellulite. The disclosed approaches can also be used to repair and reduce the appearance of cellulite in a targeted manner. Further, the disclosed proactive treatment modalities are easy and effective to use.

Some of the specific aspects of the present disclosure include one or more of focal treatment of just the septa responsible for causing dimples or depressions in the skin; minimizing bruising; accessing all treatment targets from limited, cosmetically acceptable entries; capture and retention of septa while separating the septa; intra-operative confirmation of treated target; needle-diameter sized tools for small openings; and transillumination identification of tool tip location.

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the present disclosure.

That which is claimed is:

1. A method involving a cellulite treatment system for treating expressions of cellulite on a patient's skin associated with a septa treatment site, comprising:
   gaining access to a location between tissue layers connected by septa;
   advancing the cellulite treatment system, having a mechanical septa disrupting element that cooperates with a septa hooking element, to a target site;
   deploying the septa hooking element to a first position, which shields the septa disrupting element;
   engaging selected septa to determine if the selected septa are associated with an expression of cellulite;
   transitioning the septa hooking element to a second position to expose the septa disrupting element; and
   separating certain of the selected septa that are associated with the expression of cellulite.

2. The method of claim 1, further comprising creating a treatment regimen involving using a same insertion site to treat multiple areas.

3. The method of claim 2, wherein the insertion site is located in a crease or fold in the skin when the buttocks are in a natural position.

4. The method of claim 3, wherein the insertion site is located in the crease where the buttock meets the thigh.

5. The method of claim 1, wherein the septa hooking element operates to tension selected septa.

6. The method of claim 1, further comprising employing transillumination to track positioning of the cellulite treatment device between tissue layers.

7. The method of claim 6, further comprising utilizing transillumination brightness or size of the illuminated spot on the skin to adjust the depth of a tip of the cellulite treatment system.

8. The method of claim 1, further comprising providing the cellulite treatment system with a shaft sized and shaped to be inserted within tissue and to be advanced between the tissue layers to a septa treatment site without assistance from tissue stabilizing structure applied to the patient's skin.

9. The method of claim 1, wherein the mechanical septa disrupting element includes a cutting structure, further comprising manipulating the cutting structure to cut or slice certain of the selected septa connecting tissue layers.

10. The method of claim 1, further comprising scanning skin of a subject to identify treatment areas and create a treatment regimen and a scanning data, the scanning data being stored within a computerized controller so that the efficacy of a treatment can be assessed.

11. The method of claim 1, further comprising employing a tube to remove a section of septa.

12. The method of claim 1, further comprising providing a plurality of cellulite treatment devices, combining the devices into a combined single assembly, and conducting a cellulite treatment procedure with the combined single assembly.

13. The method of claim 1, further comprising confirming that the certain of the selected septa that are associated with the expression of cellulite are separated.

14. The method of claim 1, further comprising, if septa remain intact that are associated with the expression of cellulite, engaging additional selected septa to determine if the additional selected septa area associated with an expression of cellulite; and
   separating certain of the additional selected septa that are associated with the expression of cellulite.

15. The method of claim 1, further comprising:
   advancing the septa hooking element in an undeployed position beyond the targeted site;
   wherein the engaging step comprises deploying the septa hooking element and pulling proximally to tension the septa.

16. The method claim 15, further comprising advancing the septa hooking element in an undeployed position about 1 to about 10 millimeters lateral of the targeted site.

17. The method of claim 16, further comprising advancing the septa hooking element in an undeployed position about 3 to about 6 millimeters lateral of the targeted site.

18. The method of claim 1, wherein the step of determining whether the engaged selected septa are associated with the expression of cellulite compromises pulling on the selected septa and visualizing whether a depression is formed on the skin at the target site.

19. The method of claim 18, further comprising:
   after the septa that are associated with the expression of cellulite have been separated, moving the mechanical septa disrupting element and the septa hooking element back to the undeployed position;
   advancing the septa hooking element in an undeployed position beyond the targeted site; and
   deploying the septa hooking element and pulling proximally under the targeted site to confirm that all of the septa responsible for the expression of cellulite in the targeted site have been separated.

* * * * *